United States Patent [19]

D'Ambra et al.

[11] Patent Number: 5,109,135
[45] Date of Patent: Apr. 28, 1992

[54] 2- OR 3-AMINOMETHYL-4-AMINO-3,4-DIHYDRO-2H-1,4-BENZOXAZINE INTERMEDIATES

[75] Inventors: Thomas E. D'Ambra, North Greenbush; Malcolm R. Bell, East Greenbush, both of N.Y.

[73] Assignee: Sterling Drug Inc., New York, N.Y.

[21] Appl. No.: 744,558

[22] Filed: Aug. 13, 1991

Related U.S. Application Data

[60] Division of Ser. No. 509,441, Apr. 16, 1990, Pat. No. 5,066,803, which is a division of Ser. No. 447,469, Dec. 7, 1989, Pat. No. 4,939,138, which is a continuation-in-part of Ser. No. 291,905, Dec. 29, 1988, abandoned.

[51] Int. Cl.$^5$ .................... C07D 265/36; C07D 417/06
[52] U.S. Cl. .......................... 544/73; 544/62; 544/105; 540/575
[58] Field of Search .................. 540/575; 544/73, 105, 544/62; 514/210, 218, 230.5

[56] References Cited

U.S. PATENT DOCUMENTS 4,183,938 1/1990 Rajagopalan .................. 540/546

FOREIGN PATENT DOCUMENTS 2567126 1/1986 France .

OTHER PUBLICATIONS

Kurihara et al., Chemical Abstracts, vol. 70:37748w, (1969).
Brennan and Saxton, Tetrahedron Lett. 26 (14), 1769-1772 (1985).
Tetrahedron 43 (1), 191-205 (1987); Brennan et al.

Primary Examiner—Mukund J. Shah
Assistant Examiner—Philip I. Datlow
Attorney, Agent, or Firm—Frederik W. Stonner; Paul E. Dupont

[57] ABSTRACT 2- and 3-Aminomethyl-6-arylcarbonyl-2,3-dihydropyrrolo[1,2,3-de]-1,4-benzoxazines, useful as analgesic agents, are prepared either by reaction of a 2- or 3-aminomethyl-2,3-dihydropyrrolo[1,2,3-de]-1,4-benzoxazine with an arylcarboxylic acid halide in the presence of a Lewis acid or by reaction of a 2- or 3-aminomethyl-4-amino-3,4-dihydro-2H-1,4-benzoxazine with a 1-lower-alkyl-3-aryl-1,3-diketone or with a $\beta$-aryl-$\beta$-ketopropionaldehyde under dehydrating conditions and heating the resulting hydrazone in an acid medium.

2 Claims, No Drawings

2- OR 3-AMINOMETHYL-4-AMINO-3,4-DIHYDRO-2H-1,4-BENZOXAZINE INTERMEDIATES

RELATED APPLICATIONS

This application is a division of application Ser. No. 509,441, filed Apr. 16, 1990, now U.S. Pat. No. 5,066,803, in turn a division of application Ser. No. 447,469, filed Dec. 7, 1989, now U.S. Pat. No. 4,939,138, in turn a continuation-in-part of application Ser. No. 291,905, filed Dec. 29, 1988, abandoned.

BACKGROUND OF THE INVENTION (a) Field of the Invention

This invention relates to 2- and 3-aminomethyl-6-arylcarbonyl-2,3-dihydropyrrolo[1,2,3-de]-1,4-benzoxazines which are useful as analgesic agents.

(b) Information Disclosure Statement

Brennan and Saxton, Tetrahedron Lett. 26 (14), 1769–72 (1985) and Tetrahedron 43 (1), 191–205 (1987) disclose compounds having the structures:

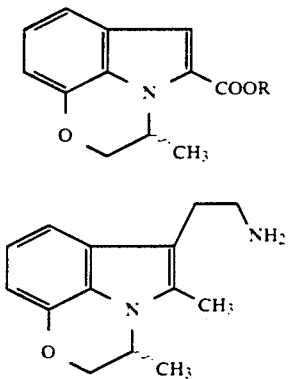

as intermediates in the total synthesis of the alkaloid obscurinervidine.

French Application 2,567,126, published Jan. 10, 1986, discloses the compound having the formula:

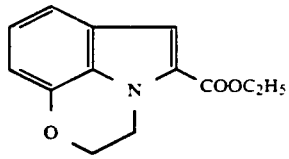

useful as an intermediate for the preparation of compounds having antidepressant activity.

Thus, so far as the inventors are aware, compounds of the 2,3-dihydropyrrolo[1,2,3-de]-1,4-benzoxazine class are not known to have utility for any purpose except as synthetic intermediates, and furthermore, so far as is known, such compounds having an arylcarbonyl function in any position or an aminoalkyl function in any position other than the 6-position are unknown.

SUMMARY

In a composition aspect, this invention relates to 5-$R_5$-R-substituted-2- and 3-aminomethyl-6-arylcarbonyl-2,3-dihydropyrrolo[1,2,3-de]-1,4-benzoxazines and their acid addition salts, which are useful as analgesic agents.

In a further composition aspect, the invention relates to R-substituted-2- and 3-aminomethyl-4-amino-3,4-dihydro-2H-1,4-benzoxazines, which are useful as intermediates for the preparation of the final products of the invention.

In a further composition aspect, the invention relates to 5-$R_5$-R-substituted-2- and 3-aminomethyl-6-phenylthio-2,3-dihydropyrrolo[1,2,3-de]-1,4-benzoxazines, which are useful as intermediates for the preparation of the final products of the invention.

In a still further composition aspect, the invention relates to 5-$R_5$-R-substituted-2- and 3-aminomethyl-2,3-dihydropyrrolo[1,2,3-de]-1,4-benzoxazines, which arae useful as intermediates for the preparation of the final products of the invention.

In a method aspect, the invention relates to a method for the relief of pain in a patient requiring such treatment comprising administering to such patient a composition containing an effective analgesic amount of a 5-$R_5$-R-substituted-2- or 3-aminomethyl-6-arylcarbonyl-2,3-dihydropyrrolo-[1,2,3-de]-1,4-benzoxazine.

In another composition aspect, the invention relates to analgesic compositions for the relief of pain comprising a pharmaceutically acceptable carrier and an effective analgesic amount of a said 5-$R_5$-R-substituted-2- or 3-aminomethyl-6-arylcarbonyl-2,3-dihydropyrrolo[1,2,3-de]-1,4-benzoxazine.

In a process aspect, the invention relates to a process for preparing a 5-$R_5$-R-substituted-2- or 3-aminomethyl-6-arylcarbonyl-2,3-dihydropyrrolo[1,2,3-de]-1,4-benzoxazine of the invention comprising reacting a 5-$R_5$-R-substituted-2- or 3-aminomethyl-2,3-dihydropyrrolo[1,2,3-de]-1,4-benzoxazine with an aryl carboxylic acid halide in the presence of a Lewis acid.

In a further process aspect, the invention relates to a process for preparing a 5-$R_5$-R-substituted-2- or 3-aminomethyl-6-arylcarbonyl-2,3-dihydropyrrolo[1,2,3-de]-1,4-benzoxazine which comprises reacting a R-substituted-2- or 3-aminomethyl-4-amino-3,4-dihydro-2H-1,4-benzoxazine with a 1-aryl-1,3-diketone or a β-aryl-β-ketopropionaldehyde, $R_5COCH_2COR_6$, under dehydrating conditions and heating the resulting hydrazone in an acid medium.

DETAILED DESCRIPTION INCLUSIVE OF THE PREFERRED EMBODIMENTS

More specifically, the invention relates to 5-$R_5$-R-substituted-2- and 3-aminomethyl-6-arylcarbonyl-2,3-dihydropyrrolo-[1,2,3-de]-1,4-benzoxazines, useful as analgesic agents, having the formula:

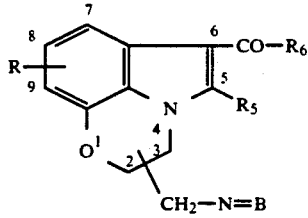

where:

R is hydrogen or from one to two substituents selected from the group consisting of lower-alkyl, lower-alkoxy, hydroxy or halogen in the 7-, 8- or 9-positions;

$R_5$ is hydrogen or lower-alkyl;

$R_6$ is phenyl, methylenedioxyphenyl (or phenyl substituted by from one to two substituents selected from the group consisting of chlorine, bromine, fluorine, lower-alkoxy, hydroxy, lower-alkyl, lower-alkylmercapto, lower-alkylsulfinyl or lower-alkylsulfonyl), 1- or 2-naphthyl (or 1- or 2-naphthyl substituted by from one to two substituents selected from the group consisting of lower-alkyl, lower-alkoxy, hydroxy, bromine, chlorine, fluorine, lower-alkylmercapto, lower-alkylsulfinyl or lower-alkylsulfonyl) or 2-, 3-, 4-, 5-, 6-, 7- or 8-quinolyl; and N=B is amino, N-lower-alkylamino, N,N-di-lower-alkylamino, 4-morpholinyl, 4-thiomorpholinyl, 1-piperidinyl, 1-pyrrolidinyl, 1-azetidinyl, 4-lower-alkyl-1-piperazinyl or 1-(hexahydro-4H-1,4-diazepinyl).

Preferred compounds of Formula I above are those where:

R is hydrogen;

$R_5$ is hydrogen or lower-alkyl;

$R_6$ is phenyl, phenyl substituted by lower-alkoxy or halogen, 1-naphthyl, 1-naphthyl substituted by halogen or 6-quinolyl; and N=B is 4-morpholinyl.

As used herein the terms lower-alkyl and lower-alkoxy mean monovalent aliphatic radicals, including branched chain radicals, of from one to four carbon atoms, for example methyl, ethyl, propyl, isopropyl, butyl, sec.-butyl, methoxy, ethoxy, propoxy, isopropoxy, butoxy or sec.-butoxy.

As used herein, the terms halo or halogen mean fluorine, chlorine or bromine.

The compounds of Formula I are prepared by the following sequence of reactions:

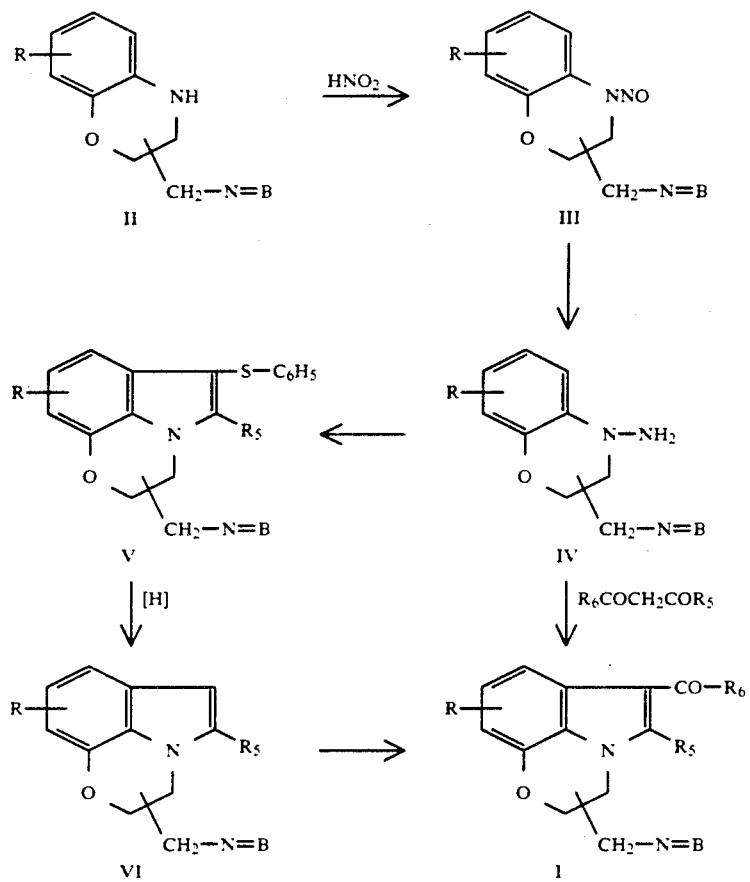

where R, $R_5$, $R_6$ and N=B have the meanings given above.

In a first step, a R-substituted-2- or 3-aminomethyl-3,4-dihydro-2H-1,4-benzoxazine of Formula II is reacted with an alkali metal nitrite in an acidic aqueous medium to produce a respective R-substituted-2- or 3-aminomethyl-4-nitroso-3,4-dihydro-2H-1,4-benzoxazine of Formula III. The reaction is carried out at a temperature from 0° C. to about 10° C. with stirring. The compounds of Formula II where R is hydrogen and N=B is 3-(4-morpholinyl), 3-(1-piperidinyl) and 3-(diethylamino) and the preparation thereof are described by Kurihara et al., Yakugaku Zasshi, 88 (9), 1118–1122 (1968); Chem. Abs., 70, 37748w (1968), the disclosure of which is incorporated herein by reference. Compounds where R and N=B have the other meanings given above can be similarly prepared.

The Kurihara et al. method of preparing the R-substituted-3-aminomethyl-3,4-dihydro-2H-1,4-benzoxazines of Formula II where N=B is, for example, 1-piperidinyl, diethylamino or 4-morpholinyl, involves reaction of an appropriate amine (HN=B) with o-nitrophenyl glycidyl ether, reduction of the resulting 1-(o-nitrophenoxy)-3-(N=B)-2-propanol with tin in the presence of a mineral acid and cyclization of the resulting 1-(o-aminophenoxy)-3-(N=B)-2-propanol with concentrated sulfuric acid. The method thus provides an unambiguous route to the 3-aminomethyl compounds uncontaminated by the isomeric 2-aminomethyl species.

The 3-aminomethyl compounds of Formula II can also be prepared by the method described by Potter and Munro, J. Het. Chem. 9, 299-301 (1972), the disclosure of which is also incorporated herein by reference. In the latter method, 2-acetamidophenol is reacted with epichlorohydrin in the presence of a strong base (sodium ethoxide). The proton on the acetamido nitrogen atom is insufficiently acidic to react with the epichlorohydrin, and the only product apparently isolated by Potter and Munro was that obtained by reaction of the epichlorohydrin at the phenolic group, i.e. 2-(2,3-epoxypropoxy) acetanilide. The latter, on treatment with sodium hydride in DMF followed by hydrolysis with dilute hydrochloric acid afforded 3-hydroxymethyl-2,3-dihydro-2H-1,4-benzoxazine uncontaminated by the isomeric 2-hydroxymethyl compound. The hydroxymethyl compound was thereafter reacted with p-toluenesulfonyl chloride in the presence of pyridine. The resulting p-toluenesulfonate can then be reacted with any desired amine, HN=B, to provide the 3-aminomethyl compounds of Formula II.

We have found that, by using 2-methanesulfonamidophenol or 2-(p-toluenesulfonamido)phenol in the Potter and Munro synthesis (the starting materials being prepared by reaction of 2-aminophenol with methanesulfonyl chloride or p-toluenesulfonyl chloride in the presence of pyridine), the proton on the sulfonamido nitrogen atom is sufficiently acidic to afford significant yields of 2-hydroxymethyl-4-methanesulfonyl- [or 4-(p-toluenesulfonyl)-]2,3-dihydro-2H-1,4-benzoxazine, resulting from initial condensation of the epichlorohydrin at the sulfonamido function followed by ring closure between the phenolic and epoxide functions, along with the isomeric 3-hydroxymethyl-4-methanesulfonyl-[or 4-(p-toluenesulfonyl)-]2,3-dihydro-2H-1,4-benzoxazine, resulting from initial condensation of the epichlorohydrin at the phenolic function followed by ring closure between the sulfonamide and epoxide functions. Conversion of the products to the p-toluenesulfonate ester as before, followed by reductive cleavage of the sulfonamide group affords the desired 2- or 3-hydroxymethyl-2,3-dihydro-2H-1,4-benzoxazine p-toluenesulfonates which, on reaction with an appropriate amine, HN=B, after separation from one another by conventional means such as fractional crystallization or chromatography, affords the 2- or 3-aminomethyl-2,3-dihydro-2H-1,4-benzoxazines of Formula II.

The compounds of Formula III are thereafter reduced to the corresponding R-substituted-2- or 3-aminomethyl-4-amino-3,4-dihydro-2H-1,4-benzoxazines of Formula IV, the reduction can be carried out either catalytically, using for example a Raney nickel or palladium-on-charcoal catalyst and hydrogen at pressures from about 30 to 50 p.s.i.g. at ambient temperature and in an inert organic solvent, for example a lower-alkanol or, alternatively, the reduction can be effected chemically with an alkali metal aluminum hydride, for example lithium aluminum hydride, or an alkali metal bis-(2-methoxyethoxy) aluminum hydride, for example sodium bis-(2-methoxyethoxy) aluminum hydride. In the latter case, the reaction is carried out in an inert organic solvent, for example tetrahydrofuran (THF), dioxane, diethyl ether, di-butyl ether or toluene at temperatures in the range from 0° C. to the boiling point of the solvent used.

The compounds of Formula IV are converted to the 5-$R_5$-R-substituted-2- or 3-aminomethyl-6-phenylthio-2,3-dihydropyrrolo[1,2,3-de]-1,4-benzoxazines of Formula V using the Fischer indole synthesis by reaction of the compounds of Formula IV with a phenylthiomethyl-$R_5$-ketone or aldehyde, $C_6H_5SCH_2COR_5$, where $R_5$ has the meanings given above. The reaction is carried out at a temperature in the range from about 20° C. to about 150° C. in an organic solvent inert under the conditions of the reaction, for example methanol, ethanol, isopropanol and the like and in the presence of an acid catalyst, for example sulfuric acid, hydrochloric acid or glacial acetic acid. It is preferred to carry out the reaction in glacial acetic acid, which not only provides the necessary acidic medium, but also serves as solvent.

Removal of the 6-phenylthio group from the compounds of Formula V to produce the 5-R -R-substituted-2-or 3-aminomethyl-2,3-dihydropyrrolo[1,2,3-de]-1,4-benzoxazines of Formula VI is effected by heating the compounds of Formula V in an organic solvent, for example a lower-alkanol, in the presence of Raney nickel at the reflux temperature of the solvent.

The final products of Formula I are prepared from the 5-$R_5$-R-substituted-2- or 3-aminomethyl-2,3-dihydropyrrolo[1,2,3-de]-1,4-benzoxazines of Formula VI by reaction of the latter with an appropriate arylcarboxylic acid halide ($R_6$CO-X, where X represents halogen) in the presence of a Lewis acid, such as aluminum chloride or ethyl aluminum chloride, and in an organic solvent inert under the conditions of the reaction. Suitable solvents are chlorinated hydrocarbons, such as methylene dichloride (hereinafter MDC) or ethylene dichloride (hereinafter EDC). The reaction is carried out at a temperature from 0° C. up to the boiling point of the solvent used.

Alternatively, as indicated by the reaction sequence above, the intermediates of Formula IV can be converted directly to the final products of Formula I by reaction of the compounds of Formula IV with a $\beta$-aryl-$\beta$-ketopropionaldehyde or a 1-aryl-1,3-diketone, $R_6COCH_2COR_5$, where $R_5$ is, respectively, hydrogen or lower-alkyl and $R_6$ has the meanings given above, using the same Fischer indole synthesis conditions described above.

It will be appreciated that the compounds of Formula I as well as the intermediates of Formulas II, III, IV, V and VI have a chiral center at the 2- or 3-positions of the respective R-substituted-2- and 3-aminomethyl-3,4-dihydro-2H-1,4-benoxazines (of Formulas II, III or IV) or the 2- or 3-positions of the 2,3-dihydropyrrolo[1,2,3-de]-1,4-benzoxazines (of Formulas I, V and VI) and thus can exist as optically active stereoisomers. Such stereoisomers of the various compounds of Formulas I, IV, V and VI are considered to be within the purview of the present invention. The isolation of either the intermediates or the final products in their optically active forms can be accomplished by application of general principles well-known in the art.

The compounds of Formulas I, IV, V and VI in free base form are converted to the acid-addition salt form by interaction of the base with an acid. In like manner, the free base can be regenerated from the acid-addition salt form in conventional manner, that is by treating the salts with cold, weak aqueous bases, for example alkali metal carbonates and alkali metal bicarbonates. The bases thus regenerated can be interacted with the same or a different acid to give back the same or a different acid-addition salt. Thus the novel bases and all of their acid-addition salts are readily interconvertible.

It will thus be appreciated that Formulas I, IV, V and VI not only represent the structural configuration of the bases of Formulas I, IV, V and VI but are also representative of the structural entities which are common to all of the compounds of Formulas I, IV, V and VI, whether in the form of the free base or in the form of the acid-addition salts of the base. It has been found that, by virtue of these common structural entities the bases of formula I and their acid-addition salts have inherent pharmacological activity of a type to be more fully described hereinbelow. This inherent pharmacological activity can be enjoyed in useful form for pharmaceutical purposes by employing the free bases themselves or the acid-addition salts formed from pharmaceutically acceptable acids, that is acids whose anions are innocuous to the animal organism in effective doses of the salts so that beneficial properties inherent in the common structural entity represented by the free bases are not vitiated by side effects ascribable to the anions.

In utilizing this pharmacological activity of the salts of the invention, it is preferred, of course, to use pharmaceutically acceptable salts. Although water insolubility, high toxicity or lack of crystalline character may make some particular salt species unsuitable or less desirable for use as such in a given pharmaceutical application, the water-insoluble or toxic salts can be converted to the corresponding pharmaceutically acceptable bases by decomposition of the salts with aqueous base as explained above, or alternatively they can be converted to any desired pharmaceutically acceptable acid-addition salt by double decomposition reactions involving the anion, for example by ion-exchange procedures.

Moreover, apart from their usefulness in pharmaceutical applications, the salts are useful as characterizing or identifying derivatives of the free bases or in isolation or purification procedures. Like all of the acid-addition salts, such characterizing or purification salt derivatives can, if desired, be used to regenerate the pharmaceutically acceptable free bases by reaction of the salts with aqueous base, or alternatively they can be converted to a pharmaceutically acceptable acid-addition salt by, for example, ion-exchange procedures.

The novel feature of the compounds of the invention, then, resides in the concept of the bases and cationic forms of the new 5-R -R-substituted-2- and 3-aminomethyl-6-arylcarbonyl-2,3-dihydropyrrolo[1,2,3-de]-1,4-benzoxazines of Formula I, the R-substituted-2- and 3-aminomethyl-4-amino-3,4-dihydro-2H-1,4-benzoxazines of Formula IV and the 5-R$_5$-R-substituted-2- and 3-aminomethyl-2,3-dihydropyrrolo-[1,2,3-de]-1,4-benzoxazines of Formulas V and VI and not in any particular acid moiety or acid anion associated with the salt forms of the compounds; rather, the acid moieties or anions which can be associated with the salt forms are in themselves neither novel nor critical and therefore can be any acid anion or acid-like substance capable of salt formation with the bases.

Thus appropriate acid-addition salts are those derived from such diverse acids as formic acid, acetic acid, isobutyric acid, alpha-mercaptopropionic acid, malic acid, fumaric acid, succinic acid, succinamic acid, tartaric acid, citric acid, lactic acid, benzoic acid, 4-methoxybenzoic acid, phthalic acid, anthranilic acid, 1-naphthalenecarboxylic acid, cinnamic acid, cyclohexanecarboxylic acid, mandelic acid, tropic acid, crotonic acid, acetylenedicarboxylic acid, sorbic acid, 2-furancarboxylic acid, cholic acid, pyrenecarboxylic acid, 2-pyridinecarboxylic acid, 3-indoleacetic acid, quinic acid, sulfamic acid, methanesulfonic acid, isethionic acid, benzenesulfonic acid, p-toluenesulfonic acid, benzenesulfinic acid, butylarsonic acid, diethylphosphonic acid, p-aminophenylarsinic acid, phenylstibnic acid, phenylphosphinous acid, methylphosphinic acid, phenylphosphinic acid, hydrofluoric acid, hydrochloric acid, hydrobromic acid, hydriodic acid, perchloric acid, nitric acid, sulfuric acid, phosphoric acid, hydrocyanic acid, phosphotungstic acid, molybdic acid, phosphomolybdic acid, pyrophosphoric acid, arsenic acid, picric acid, picrolonic acid, barbituric acid, boron trifluoride and the like.

The acid-addition salts are prepared by reacting the free base and the acid in an organic solvent and isolating the salt directly or by concentration of the solution.

In standard pharmacological test procedures, the compounds of Formula I have been found to possess analgesic activity and are thus useful as analgesic agents.

The test procedures used to determine the analgesic activities of the compounds have been described in detail in the prior art and are as follows: The acetylcholine-induced abdominal constriction test, which is a primary analgesic screening test designed to measure the ability of a test agent to suppress acetylcholine-induced abdominal constriction in mice, described by Collier et al., Brit. J. Pharmacol. Chemotherap. 32, 295 (1968); a modification of the anti-bradykinin test, which is also a primary analgesic screening procedure, described by Berkowitz et al., J. Pharmacol. Exptl. Therap 177, 500–508 (1971), Blane et al., J. Pharm. Pharmacol 19, 367–373 (1967), Botha et al., Eur. J. Pharmacol. 6, 312–321 (1969) and Deffenu et al., J. Pharm. Pharmacol. 18, 135 (1966); the rat paw flexion test, described by Kuzuna et al., Chem. Pharm. Bull., 23, 1184–1191 (1975), Winter et al., J. Pharm. Exptl. Therap., 211, 678–685 (1979) and Capetola et al., J. Pharm. Exptl. Therap. 214, 16–23 (1980); and the mouse vas deferens adrenergic transmission test, described by Henderson et al., Brit. J. Pharmacol., 46, 764–766 (1972).

In order to further detail the analgesic profiles of the compounds of the invention, their activities in the inhibition of acetic acid-induced writhing assay in the rat, the inhibition of cyclooxygenase assay and a modification of the Randall-Selitto analgesic test were also determined. The test procedure used to determine the inhibition of acetic acid-induced writhing in the rat is described as follows.

Male Sprague Dawley rats (Taconic Farms) weighing between 160 and 200g were treated in a random and blind fashion with 1% gum tragacanth vehicle or test agent suspended or dissolved in 1% gum tragacanth. Rats were individually housed in plastic cages (28×18×12 cm) throughout the experiment. Forty-five minutes after drug treatment, 0.5 ml of 9% (w/v) acetic acid was administered intraperitoneally, and animals were returned to their cages for 10 minutes. Writhing is not normally seen during this 10 minute period. Each animal was then observed for a writhing response during a subsequent 10 minute interval (55–65 minutes post-drug treatment). A writhing response was defined as arching of the back with extension of the hindlimbs and contraction of abdominal muscles. The number of writhing responses exhibited by each animal was recorded and the mean ±SE for each experimental group was calculated. Data were expressed as percent inhibition of the mean number of writhes in the vehicle treated control group. Data were evaluated for statistical significance by Dunnett's test, and $ED_{50}$'s for inhibition of acetic acid-induced writhing were determined by the graded dose-response analysis of Tallarida and Murray, Manual of Pharmacologic Calculations with Computer Programs, Springer Verlag, New York (1981).

The test procedure used to determine cyclooxygenase inhibitory activity is described as follows.

Male mice were decapitated and stomach and brain (cerebral cortex, hypothalamus and medulla) were rapidly dissected over ice. The brains were homogenized in 3 volumes of ice cold 0.1 M potassium phosphate buffer, pH 7.4 containing 10 mM EDTA and 1% BSA (w/v). The homogenate was centrifuged at 10,000 xg for 15 minutes. The resulting supernatant was decanted and centrifuged at 100,000 xg for 60 minutes yielding a crude microsomal pellet. The pellet was washed superficially three times in 3 volumes of 0.1 M potassium phosphate buffer before final resuspension in 1.5 volumes of 0.1 M potassium phosphate buffer containing 1 mM norepinephrine and 1 mM reduced glutathione. The microsomes (50 $\mu$l) were preincubated with 50 $\mu$l of indomethacin (0.3 $\mu$M), test compound or norepinephrine/glutathione-containing buffer for 5 minutes at room temperature. The enzyme reaction was initiated by the addition of 50 $\mu$l of $^{14}$C arachidonic acid to yield a final concentration of 10 $\mu$M. After a further incubation of 15 minutes at 37° C., the reaction was stopped by the addition of 50 $\mu$l of 4M formic acid. Blank values were determined by using microsomes boiled for 5 minutes but otherwise were treated similarly. The $^{14}$C-labelled material was extracted 3 times with 0.5 ml of ethyl acetate with intermediate centrifugations at 500 xg for 5 minutes to clarify the aqueous and organic phases. This procedure extracted >95% of the $^{14}$C-labelled materials. The ethyl acetate washes were added to tubes containing 5 $\mu$g each of $PGE_2$, $PGF_2$, $PGD_2$, and 10 $\mu$g $PGI_2$ in 25 $\mu$l of ethanol. The mixture was evaporated to dryness under nitrogen and the residue dissolved in 150 $\mu$l of chloroform:methanol (2:1). This solution was spotted on 5×20 cm silica gel plates and chromatographed with an ethyl acetate, trimethylpentane, acetic acid and water mixture (110:50:20:100 by volume) prepared by shaking the solvents and separating and discarding the organic phase. The prostaglandins were visualized in iodine vapor, the various spots were scraped, and the $^{14}$C-labelled prostaglandins quantitated by liquid scintillation spectroscopy in 10 ml of BIOFLUOR® or FLUORODYNE®.

The modification of the Randall-Selitto analgesic test procedure used is described as follows:

Female Sprague-Dawley rats, weighing 60 to 95 grams, were routinely used. In three experiments, male Sprague-Dawley rats of comparable weights were used. The rats were housed 10 per cage with food and water available ad libitum.

The Randall-Selitto Test device used was a UGO Basile Analgesy Meter (catalog no. 7200), with the flat-topped plinth on the bottom, acting as a platform upon which the hind paw of the rat was placed and the round-pointed pusher oriented downward. The gap between the pusher and the plinth was set at the thickness of approximately 0.1 cm for normal paws and approximately 0.2 cm for inflamed paws. After placing the hind paw on the plinth, gradually increasing pressure was applied to the paw by a motor-driven weight sliding along a calibrated scale.

Testing was accomplished by holding the rat upright in one hand by the scruff of the neck, then guiding the test paw into position on the plinth, under the pusher. The paw was positioned so that the pusher made contact with it at a point where the metatarsals and phalanges meet, between the third and fourth digits. Application of gradually increasing force to the paw was accomplished by operating the device with a foot pedal.

A rat was considered to have responded to the pressure (pain stimulus) if it reacted in any one of the following ways:

1. if the rat pulled the paw free of the test device;
2. if the rat began to struggle in such a way that the operator would have difficulty holding onto it; or
3. if the rat vocalized.

The test involved a total of sixty rats, which were prescreened in the following manner. Both paws of each naive rat were tested twice as described above. The first test acclimatized the animal to the apparatus; the second established a baseline response for comparison with later inflamed-paw responses. Any rat responding to less than 60 grams of pressure during this second trial of the left paw was discarded and replaced.

Hyperalgesia was induced by administration of brewers' yeast (Fisher Scientific Company, Lot 785660) 20% suspension in 0.85% saline. Each of the rats selected as described above was given a 0.1 cc sub-plantar injection of this suspension in the left paw, using a 23 gauge, 1 inch needle.

Animals were given the test drug, p.o., two hours after the sub-plantar injection, four doses customarily being given, along with vehicle control and a positive control (Zomepirac). Ten animals were used in each experimental group. Treatments were assigned in such a way that both the range and the means of the baseline readings were as nearly equal as possible for all treatments.

Final testing was performed two hours after the administration of the test drug. The observer was unaware of the treatment any particular rat had received. In this portion of the study, all the inflamed (left) paws were tested first, as a group, and then the non-inflamed (right) paw was tested.

Results were analyzed with the Student's t-test. The minimally effective dose was defined as the lowest dose tested which met 2 criteria: i) did not produce a response significantly ($>0.05$) different from the second (baseline) preliminary reading, and ii) permitted application of significantly ($p<0.05$) greater pressure than that observed for the hyperalgesic response in vehicle-treated rats. Thus, the dose had to completely antagonize the hyperalgesia.

The compounds of formula I of the invention can be prepared for pharmaceutical use by incorporating them in unit dosage form as tablets or capsules for oral or parenteral administration either alone or in combination with suitable adjuvants such as calcium carbonate, starch, lactose, talc, magnesium stearate, gum acacia and the like. Still further, the compounds can be formulated for oral or parenteral administration either in aqueous solutions of the water soluble salts or in aqueous alcohol, glycol or oil solutions or oil-water emulsions in the same manner as conventional medicinal substances are prepared.

The percentages of active component in such compositions may be varied so that a suitable dosage is obtained. The dosage administered to a particular patient is variable, depending upon the clinician's judgment using as criteria: the route of administration, the duration of treatment, the size and the physical condition of the patient, the potency of the active component and the patient's response thereto. An effective dosage amount of the active component can thus only be determined by the clinician after a consideration of all criteria and using his best judgment on the patient's behalf.

The molecular structures of the compounds of the invention were assigned on the basis of study of their infrared, ultraviolet and NMR spectra. The structures were confirmed by the correspondence between calculated and found values for elementary analyses for the elements.

The following examples will further illustrate the invention without, however, limiting it thereto. All melting points are uncorrected.

EXEMPLARY DISCLOSURE

PREPARATION OF INTERMEDIATES

Preparation 1—The Compounds of Formula II

A. The compounds of Formula II can be prepared using the method described by Kurihara et al. ibid. The procedure used for the preparation of 3-(4-morpholinylmethyl)-3,4-dihydro-2H-1,4-benzoxazine was as follows.

A five liter round bottom flask was charged with 163 g (1.0 mole) of o-nitrophenol (15% moisture content) and 193 g (1.4 moles) of potassium carbonate in 1.5 liters of DMF. The reaction mixture was heated on a steam bath for 30 minutes, treated with 176 ml (2.25 moles) of epichlorohydrin added rapidly in three portions and then heated with stirring for an additional 2 hours. The reaction mixture was then cooled to room temperature, filtered to remove a solid, and the filtrate concentrated in vacuo. The residual dark oil was taken into ethyl acetate, the solution washed with brine, and the organic phase was separated, dried over magnesium sulfate and concentrated in vacuo. The resulting solid was suspended in 750 ml of diethyl ether and stirred overnight. The insoluble material was removed by filtration, and the filtrate was diluted with hexane to give three crops of product (139.9 g) consisting of 2-(1,2-epoxy-3-propyloxynitrobenzene.

The resulting product (133 g, 0.68 mole) was added to a two liter round bottom flask containing 133 ml (1.53 moles) of morpholine and 750 ml of toluene. The reaction mixture was stirred for 2 hours at 95° C., then overnight at room temperature and then concentrated in vacuo to afford a yellow oil which was dissolved in ethyl acetate. The resulting solution was washed with brine, dried over magnesium sulfate and concentrated in vacuo, the residual morpholine being removed under high vacuum (0.2 mm) at 70° C. The residual oil was crystallized from 400 ml of diethyl ether to give two crops, totalling 160.3 g, of 2-[3-(4-morpholinyl)-2-hydroxy-1-propyloxy]nitrobenzene.

A five liter round bottom flask was charged with 63.8 ml (0.45 mole) of trifluoroacetic anhydride and 400 ml of MDC under nitrogen. The resulting solution was cooled to −65° C. with a dry ice bath, treated with 42.6 g (0.54 mole) of dimethylsulfoxide over a period of 15 minutes, stirred for 30 minutes, and then treated with a solution of 90 g (0.32 mole) of 2-[3-(4-morpholinyl)-2-hydroxy-1-propyloxy]nitrobenzene in 200 ml of MDC over a 35 minute period. The reaction mixture was stirred for 30 minutes, quenched with 261 ml of diisopropylethylamine, the reaction temperature allowed to rise to −10° C. and the mixture treated with one liter of diethyl ether. The pale yellow solid which separated was collected by filtration, slurried in 1.5 liters of diethyl ether and the product collected and dried to give 73.7 g of 2-[3-(4-morpholinyl)-2-keto-1-propyloxy]nitrobenzene.

The product (20.4 g, 0.73 mole) and 5 g of 5% platinum on carbon sulfided was placed in a two liter stirrable Parr pressure reactor under nitrogen containing 1 liter of ethyl acetate. The reactor was pressurized to 100 psi of hydrogen and stirred for 20 hours. The catalyst was then removed by filtration, the filtrate treated with 14 g of oxalic acid dihydrate, and the salt which separated was collected by filtration and then neutralized with a solution of sodium bicarbonate. The mixture was extracted with ethyl acetate, and the organic solution was dried over magnesium sulfate and concentrated in vacuo to give 9.3 g of 3-(4-morpholinylmethyl)-3,4-dihydro-2H-1,4-benzoxazine, m.p. 117°–121° C.

The 3-(4-morpholinylmethyl)-3,4-dihydro-2H-1,4-benzoxazine described above was resolved into its d- and l-enantiomers as follows:

The racemic material (45.5 g, 0.19 mole) was dissolved in 600 ml of hot acetone, and 70 g (0.19 mole) of d-dibenzoyltartaric acid monohydrate was added and the mixture stirred until all material had dissolved. The solution was then concentrated to about 200 ml, diluted with 500 ml of ethyl acetate and cooled. The solid which separated was collected and dried to give 36 g of the crude l-base.d-acid salt, the filtrate being set aside for further processing. Several recrystallizations of the crude salt from methanol afforded 6.3 g of (−)-3-(4-morpholinylmethyl)-3,4-dihydro-2H-1,4-benzoxazine-.(+)-dibenzoyltartrate $[\alpha]_D^{25} = +45.8°$ (1% in DMF), m.p. 176°–178° C.

The latter (26.9 g) was partitioned between ethyl acetate and saturated aqueous sodium carbonate, and the organic layer was dried over magnesium sulfate, filtered and taken to dryness to yield 15.1 g of a white solid which was recrystallized from ethyl acetate/hexane to give 6.7 g of (−)-3-(4-morpholinylmethyl)-3,4-dihydro-2H-1,4-benzoxazine, $[\alpha]_D^{25} = -28.0°$ (1% in CHCl$_3$), m.p. 93°–95° C.

The filtrate set aside from the preparation of the l-base.d-acid salt as described above was combined with all the other liquors from the recrystallizations thereof and partitioned between ethyl acetate and aqueous sodium carbonate, and the organic layer was dried over magnesium sulfate, filtered and taken to dryness. The residue (13.7 g, 0.059 mole) was dissolved in methanol, 22 g (0.059 mole) of (−)-dibenzoyltartaric acid monohydrate was added and the solution diluted with hexane. The solid which separated was collected and recrystallized from methanol to give the 2:1 salt of (+)-3-(4-morpholinylmethyl)-3,4-dihydro-2H-1,4-benzoxazine (−)-dibenzoyltartrate, $[\alpha]_D^{25} = -39.8°$ (1% in DMF), m.p. 177.5°–179.5° C. Another batch, prepared similarly, showed $[\alpha]_D^{25} = -42.0°$ (1% in DMF).

The free base was liberated from 31.6 g of the latter by partitioning the salt between ethyl acetate and saturated sodium carbonate and isolation of the base from the organic layer. Recrystallization of the product thus obtained from ethyl acetate/hexane afforded 9.4 g of (+)-3-(morpholinylmethyl)-3,4-dihydro-2H-1,4-benzoxazine. $[\alpha]_D^{25} = +28.1°$ (1% in CHCl$_3$), m.p. 94°-96° C.

Proceeding in a manner similar to that described above in Preparation 1A and by Kurihara et al., substituting for the 2-nitrophenyl glycidyl ether used by Kurihara et al., a molar equivalent amount of 6-methoxy-2-nitrophenyl glycidyl ether or 6-chloro-2-nitrophenyl glycidyl ether and substituting for the piperidine, diethylamine or morpholine used by Kurihara et al. a molar equivalent amount of ammonia, methylamine, thiomorpholine, pyrrolidine, azetidine, 1-methylpiperazine or hexahydro-4H-1,4-diazepine, there can be obtained 8-methoxy-3-aminomethyl-3,4-dihydro-2H-1,4-benzoxazine, 8-methoxy-3-methylaminomethyl-3,4-dihydro-2H-1,4-benzoxazine, 8-methoxy-3-(4-thiomorpholinylmethyl)-3,4-dihydro-2H-1,4-benzoxazine, 8-methoxy-3-(1-pyrrolidinylmethyl)-3,4-dihydro-2H-1,4-benzoxazine, 8-methoxy-3-(1-azetidinylmethyl)-3,4-dihydro-2H-1,4-benzoxazine, 8-methoxy-3-(4-methyl-1-piperazinylmethyl)-3,4-dihydro-2H-1,4-benzoxazine, 8-methoxy-3-[1-(hexahydro-4H-1,4-diazepinyl)methyl]-3,4-dihydro-2H-1,4-benzoxazine, 8-chloro-3-aminomethyl-3,4-dihydro-2H-1,4-benzoxazine, 8-chloro-3-methylaminomethyl-3,4-dihydro-2H-1,4-benzoxazine, 8-chloro-3-(4-thiomorpholinylmethyl)-3,4-dihydro-2H-1,4-benzoxazine, 8-chloro-3-(1-pyrrolidinylmethyl)-3,4-dihydro-2H-1,4-benzoxazine, 8-chloro-3-(1azetidinylmethyl)-3,4-dihydro-2H-1,4-benzoxazine, 8-chloro-3-(4-methyl-1-piperazinylmethyl)-3,4-dihydro-2H-1,4-benzoxazine and 8-chloro-3-[1-(hexahydro-4H-1,4-diazepinyl)methyl]-3,4-dihydro-2H-1,4-benzoxazine.

B. To a stirred suspension of 109 g (1.0 mole) of 2-aminophenol in 1 liter of MDC containing 79 g of pyridine was added, over a 20 minute period with stirring and while maintaining the temperature below 38° C., 115 g (1.0 mole) of methanesulfonyl chloride. When addition was complete the reaction mixture was washed with water, then with saturated sodium bicarbonate and the organic solution taken to dryness and the residue diluted with xylene and taken to dryness again to remove residual pyridine. There was thus obtained 106 g of 2-methanesulfonamidophenol.

The latter (10 g, 0.053 mole) was dissolved in 40 ml of N-methylpyrrolidone containing 4.0 g (0.06 mole) of solid potassium hydroxide, and the mixture was treated over a five minute period while warming on a steam bath with 10 ml (0.127 mole) of epichlorohydrin. The mixture was extracted with isopropyl acetate, and the organic extracts were washed two times with water, dried and the organic layer taken to dryness to give 15 g of a mixture of 2- and 3-hydroxymethyl-4-methanesulfonyl-3,4-dihydro-2H-1,4-benzoxazine.

The crude product (about 120 g, 0.5 mole) was dissolved in 1 liter of MDC, cooled to 10° C. in an ice bath and treated first with 125 ml of triethylamine followed by a solution of 97 g (0.5 mole) of p-toluenesulfonyl chloride in 200 ml of MDC. The reaction mixture was stirred at ambient temperature for about twelve hours and then washed first with water, then with saturated sodium carbonate and taken to dryness. The residue was dissolved in toluene, the solution washed again with water, dried and taken to near dryness, and the residue was diluted with diethyl ether and filtered. The solid material was rinsed with diethyl ether, then triturated with methanol and collected and dried to give 113 g of crude product consisting of a mixture of 2- and 3-hydroxymethyl-4-methanesulfonyl-3,4-dihydro-2H-1,4-benzoxazine p-toluenesulfonate. The latter was recrystallized from 150 ml of MDC to give 47 g of 3-hydroxymethyl-4-methanesulfonyl-3,4-dihydro-2H-1,4-benzoxazine p-toluenesulfonate. The mother liquors from the latter crystallization were set aside, allowed to cool for about twelve hours, and the solid which separated was collected by filtration and dried to give 19 g of 2-hydroxymethyl-4-methanesulfonyl-3,4-dihydro-2H-1,4-benzoxazine p-toluenesulfonate.

A solution of 18.5 g (0.047 mole) of 2-hydroxymethyl-4-methanesulfonyl-3,4-dihydro-2H-1,4-benzoxazine p-toluenesulfonate in 40 ml of N-methylpyrrolidone and 50 ml of morpholine was heated under reflux for about one and a half hours and then taken to dryness. The residue was extracted with ethyl acetate, and the solution was washed first with water, then with brine and taken to dryness to give 15 g of an oil which crystallized on standing. The solid was triturated with diethyl ether and collected by filtration to give 11.1 g of 2-(4-morpholinylmethyl)-4-methanesulfonyl-3,4-dihydro-2H-1,4-benzoxazine.

To a stirred solution of 10.8 g (0.035 mole) of the latter in 100 ml of toluene at ambient temperature was added dropwise and with stirring over a twenty minute period a solution of 8 g (0.040 mole) of a 70% solution of sodium bis-(2-methoxyethoxy)aluminum hydride in toluene. The mixture was stirred for thirty minutes at ambient temperature, warmed on a steam bath for five minutes, cooled, quenched with water and 35% sodium hydroxide, and extracted with toluene. The combined organic extracts were washed with water, dried and taken to dryness to give the crude product as a syrup which was chromatographed on silica gel, the product being eluted with 40:60 ethyl acetate:hexane. There was thus obtained 8 g of 2-(4-morpholinylmethyl)-3,4-dihydro-2H-1,4-benzoxazine.

In the same manner, the isomeric 3-hydroxymethyl-4-methanesulfonyl-3,4-dihydro-2H-1,4-benzoxazine p-toluenesulfonate obtained above (40.8 g, 0.10 mole) was reacted with 60 ml of morpholine in 100 ml of N-methylpyrrolidone to give 22.5 g of 3-(4-morpholinylmethyl)-4-methanesulfonyl-3,4-dihydro-2H-1,4-benzoxazine.

The latter (22 g, 0.07 mole), on reduction with 56.5 g (0.28 mole) of a 70% solution of sodium bis-(2-methoxyethoxy) aluminum hydride in toluene, gave 11.8 g of 3-(4-morpholinylmethyl)-3,4-dihydro-2H-1,4-benzoxazine.

Proceeding in a manner similar to that described above in Preparation 1B for the preparation of 2-(4-morpholinylmethyl)-3,4-dihydro-2H-1,4-benzoxazine by reaction of 2-hydroxymethyl-4-methanesulfonyl-3,4-dihydro-2H-1,4-benzoxazine p-toluenesulfonate with morpholine and reduction of the resulting 2-(4-morpholinylmethyl)-4-methanesulfonyl-3,4-dihydro-2H-1,4-benzoxazine with sodium bis-(2-methoxyethoxy) aluminum hydride, substituting for the morpholine used therein a molar equivalent amount of piperidine, diethylamine, ammonia, methylamine, thiomorpholine, pyrrolidine, azetidine, 1-methylpiperazine or hexahydro-4H-1,4-diazepine, there can be obtained, respectively, 2-(1-piperidinylmethyl)-3,4-dihydro-2H-1,4-benzoxazine, 2-(N,N-diethylaminomethyl)-3,4-dihydro-2H-1,4-benzoxazine, 2-aminomethyl-3,4-dihydro-2H-1,4-benzoxazine, 2-methylaminomethyl-3,4-dihydro-2H-1,4-benzoxazine, 2-(4-thiomorpholinylmethyl)3,4-dihydro- 2H-1,4-benzoxazine, 2-(1-pyrrolidinylmethyl)-3,4-dihydro-2H-1,4-benzoxazine, 2-(1-azetidinylmethyl)-3,4-dihydro-2H-1,4-benzoxazine, 2-(4-methyl-1-piperazinylmethyl)-3,4-dihydro-2H-1,4-benzoxazine or 2-[1-(hexahydro-4H-1,4-diazepinyl)-methyl]-3,4-dihydro-2H-1,4-benzoxazine.

Preparation 2 - The Compounds of Formula III

A. A solution of (−)-3-(4-morpholinylmethyl)-3,4-dihydro-2H-1,4-benzoxazine in 250 ml of 2N aqueous hydrochloric acid was cooled to 0° C. and treated with a solution of 4.8 g (0.070 mole) of sodium nitrite in 50 ml of water. The solution was stirred for one hour at 0° C., poured into a mixture of 1500 ml of water and 1 liter of ethyl acetate and neutralized carefully by the addition of solid sodium bicarbonate. The organic layer was separated, and the aqueous layer was extracted with an additional 400 ml of ethyl acetate. The combined organic extracts were dried over magnesium sulfate, filtered and taken to dryness to give (−)-3-(4-morpholinylmethyl)-4-nitroso-3,4-dihydro-2H-1,4-benzoxazine, which was used as such in the next synthetic step without further purification or characterization.

Similarly 17.4 g (0.074 mole) of (+)-3-(4-morpholinylmethyl)-3,4-dihydro-2H-1,4-benzoxazine in 300 ml of 2N aqueous hydrochloric acid was treated with 5.6 g (0.081 mole) of sodium nitrite in 60 ml of water at 0° C. to produce (+)-3-(4-morpholinylmethyl)-4-nitroso-3,4-dihydro-2H-1,4-benzoxazine, which was used as such in the next synthetic step without further purification or characterization.

Similarly 10.9 g (0.047 mole) of racemic 3-(4-morpholinylmethyl)-3,4-dihydro-2H-1,4-benzoxazine in 250 ml of 2N aqueous hydrochloric acid was treated with 3.9 g (0.057 mole) of sodium nitrite in 50 ml of water at 0° C. to produce racemic 3-(4-morpholinylmethyl)-4-nitroso-3,4-dihydro-2H-1,4-benzoxazine, which was used as such in the next synthetic step without further purification or characterization.

B. Similarly 8 g (0.034 mole) of racemic 2-(4-morpholinylmethyl)-3,4-dihydro-2H-1,4-benzoxazine in about 130 ml. of 2N aqueous hydrochloric acid was treated with 1.3 g (0.019 mole) of sodium nitrite in about 100 ml of water at 0° C. to produce racemic 2-(4-morpholinylmethyl)-4-nitroso-3,4-dihydro 2H 1,4-benzoxazine, which was used as such in the next synthetic step without further purification or characterization.

Proceeding in a manner similar to that described above in Preparation 2A, substituting for the (+) or (−)-3-(4-morpholinylmethyl)-3,4-dihydro-2H-1,4-benzoxazine used therein a molar equivalent amount of 3-(1-piperidinylmethyl)-3,4-dihydro-2H-1,4-benzoxazine (Kurihara et al.), 3-(N,N-diethylaminomethyl)-3,4-dihydro-2H-1,4-benzoxazine (Kurihara et al.), 8-methoxy-3-aminomethyl-3,4-dihydro-2H-1,4-benzoxazine, 8-methoxy-3-methylaminomethyl-3,4-dihydro-2H-1,4-benzoxazine, 8-methoxy-3-(4-thiomorpholinylmethyl)-3,4-dihydro-2H-1,4-benzoxazine, 8-methoxy-3-(1-pyrrolidinylmethyl)-3,4-dihydro-2H-1,4-benzoxazine, 8-methoxy-3-(1-azetidinylmethyl)-3,4-dihydro-2H-1,4-benzoxazine, 8-methoxy-3-(4-methyl-1-piperazinylmethyl)-3,4-dihydro-2H-1,4-benzoxazine, 8-methoxy-3-[1-(hexahydro-4H-1,4-diazepinyl)methyl]-3,4-dihydro-2H-1,4benzoxazine, 8-chloro-3-aminomethyl-3,4-dihydro-2H-1,4-benzoxazine, 8-chloro-3-methylaminomethyl-3,4-dihydro-2H-1,4-benzoxazine, 8-chloro-3-(4-thiomorpholinylmethyl)-3,4-dihydro-2H-1,4-benzoxazine, 8-chloro-3-(1-pyrrolidinylmethyl)-3,4-dihydro- 2H-1,4-benzoxazine, 8-chloro-3-(1-azetidinylmethyl)-3,4-dihydro-2H-1,4-benzoxazine, 8-chloro-3-(4-methyl-1-piperazinylmethyl)-3,4-dihydro-2H-1,4-benzoxazine and 8-chloro-3-[1-(hexahydro-4H-1,4-diazepinyl)methyl]-3,4-dihydro-2H-1,4-benzoxazine, there can be obtained, respectively, 3-(1-piperidinylmethyl)-4-nitroso-3,4-dihydro-2H-1,4-benzoxazine, -(N,N-diethylaminomethyl)-4-nitroso-3,4-dihydro-2H-1,4-benzoxazine, 8-methoxy-3-aminomethyl-4-nitroso-3,4-dihydro-2H-1,4-benzoxazine, 8-methoxy-3-methylaminomethyl-4-nitroso-3,4-dihydro-2H-1,4-benzoxazine, 8-methoxy-3-(4-thiomorpholinylmethyl)-4-nitroso-3,4-dihydro-2H-1,4-benzoxazine, 8-methoxy-3-(1-pyrrolidinylmethyl)-4-nitroso-3,4-dihydro-2H-1,4-benzoxazine, 8-methoxy-3-(1-azetidinylmethyl)-4-nitroso-3,4-dihydro-2H-1,4-benzoxazine, 8-methoxy-3-(4-methyl-1-piperazinylmethyl)-4-nitroso-3,4-dihydro-2H-1,4-benzoxazine, 8-methoxy-3-[1-(hexahydro-4H-1,4-diazepinyl)methyl]-4-nitroso-3,4-dihydro-2H-1,4-benzoxazine, 8-chloro-3-aminomethyl-4-nitroso-3,4-dihydro-2H-1,4-benzoxazine, 8-chloro-3-methylaminomethyl-4-nitroso-3,4-dihydro-2H-1,4-benzoxazine, 8-chloro-3-(4-thiomorpholinylmethyl)-4-nitroso-3,4-dihydro-2-H-1,4-benzoxazine, 8-chloro-3-(1-pyrrolidinylmethyl)-4-nitroso-3,4-dihydro-2H-1,4-benzoxazine, 8-chloro-3-(1-azetidinylmethyl)-4-nitroso-3,4-dihydro-2H-1,4-benzoxazine, 8-chloro-3-(4-methyl-1-piperazinylmethyl)-4-nitroso-3,4-dihydro-2H-1,4-benzoxazine and 8-chloro-3-[1-(hexahydro-4H-1,4-diazepinyl)methyl]-4-nitroso-3,4-dihydro-2H-1,4-benzoxazine.

Proceeding in a manner similar to that described in Preparation 2B above, substituting for the 2-(4-morpholinylmethyl)-3,4-dihydro-2H-1,4-benzoxazine used therein a molar equivalent amount of 2-(1-piperidinylmethyl)-3,4-dihydro-2H-1,4-benzoxazine, 2-(N,N-diethylaminomethyl)-3,4-dihydro-2H-1,4-benzoxazine, 2-aminomethyl-3,4-dihydro-2H-1,4-benzoxazine, 2-methylaminomethyl-3,4-dihydro-2H-1,4-benzoxazine, 2-(4-thiomorpholinylmethyl)-3,4-dihydro-2H-1,4-benzoxazine, 2-(1-pyrrolidinylmethyl)-3,4-dihydro-2H-1,4-benzoxazine, 2-(1-azetidinylmethyl)-3,4-dihydro-2H-1,4-benzoxazine, 2-(4-methyl-1-piperazinylmethyl)-3,4-dihydro-2H-1,4-benzoxazine or 2-[1-(hexahydro-4H-1,4-diazepinyl)-methyl]-3,4-dihydro-2H-1,4-benzoxazine, there can be obtained, respectively, 2-(1-piperidinylmethyl)-4-nitroso-3,4-dihydro-2H-1,4-benzoxazine, 2-(N,N-diethylaminomethyl)-4-nitroso-3,4-dihydro-2H-1,4-benzoxazine, 2-aminomethyl-4-nitroso-3,4-dihydro-2H-1,4-benzoxazine, 2-methylaminomethyl-4-nitroso-3,4-dihydro-2H-1,4-benzoxazine, 2-(4-thiomorpholinylmethyl)-4-nitroso-3,4-dihydro-2H-1,4-benzoxazine, 2-(1-pyrolidinylmethyl)-4-nitroso-3,4-dihydro-2H-1,4-benzoxazine, 2-(1-azetidinylmethyl)-4-nitroso-3,4-dihydro-2H-1,4-benzoxazine, 2-(4-methyl-1-piperazinylmethyl)-4-nitroso-3,4-dihydro-2H-1,4-benzoxazine or 2-[1-(hexahydro-4H-1,4-diazepinyl)methyl]-4-nitroso-3,4-dihydro-2H-1,4-benzoxazine.

Preparation 3 - The Compounds of Formula IV

A. To a suspension of 56 g of lithium aluminum hydride in 500 ml of THF was added the (−)-3-(4-morpholinylmethyl)- 4-nitroso-3,4-dihydro-2H-1,4-benzoxazine described above while cooling the reaction mixture to 0° C. with an external cooling bath. When addition was complete the cooling bath was removed, the reaction mixture was stirred for one hour at ambient temperature, cooled again to 0° C. and the excess hydride carefully quenched by the dropwise addition of 5 ml of water, followed by 8 ml of 10% aqueous sodium hydroxide, followed by an additional 5 ml of water. The mixture was stirred, filtered through filter aid, and the filtrate taken to dryness to afford 14.3 g of (−)-3-(4-morpholinylmethyl)-4-amino-3,4-dihydro-2H-1,4-benzoxazine, which was used as such in the next synthetic step without further characterization or purification.

Similarly the crude (+) (0.074 mole) and racemic (0.047 mole) 3-(4-morpholinylmethyl)-4-nitroso-3,4-dihydro-2H-1,4-benzoxazines described above were reduced with lithium aluminum hydride in THF to give the corresponding (+) and racemic 3-(4-morpholinylmethyl)-4-amino-3,4-dihydro-2H-1,4-benzoxazines, (15.5 g, 0.062 mole and 8.8 g, 0.035 mole, respectively) which were used as such in the next step without further characterization or purification.

B. To a solution of 16 g (0.055 mole) of a 70% solution of sodium bis-(2-methoxyethoxy) aluminum hydride diluted with 75 ml of toluene was added with stirring at 0° C. over a thirty minute period a solution of 2-(4-morpholinylmethyl)-4-nitroso-3,4-dihydro-2H-1,4-benzoxazine in 80 ml of toluene. The mixture was stirred at ambient temperature for two hours, then quenched by the dropwise addition of 1N sodium hydroxide. The organic layer was washed with additional 1N sodium hydroxide, then with water, dried and taken to dryness to give 7.8 g of a syrup which was chromatographed on silica gel to give 4.6 g of 2-(4-morpholinylmethyl)-4-amino-3,4-dihydro-2H-1,4-benzoxazine.

Following a procedure similar to that described above in Preparation 3A, substituting for the (−)-3-(4-morpholinylmethyl)-4-nitroso-3,4-dihydro-2H-1,4-benzoxazine used therein a molar equivalent amount of 3-(1-piperidinylmethyl)-4-nitroso-3,4-dihydro-2H-1,4-benzoxazine, 3-(N,N-diethylaminomethyl)-4-nitroso-3,4-dihydro-2H-1,4-benzoxazine, 8-methoxy-3-aminomethyl-4-nitroso-3,4-dihydro-2H-1,4-benzoxazine, 8-methoxy-3-methylaminomethyl-4-nitroso-3,4-dihydro-2H-1,4-benzoxazine, 8-methoxy-3-(4-thiomorpholinylmethyl)-4-nitroso-3,4-dihydro-2H-1,4-benzoxazine, 8-methoxy-3-(1-pyrrolidinylmethyl)-4-nitroso-3,4-dihydro-2H-1,4-benzoxazine, 8-methoxy-3-(1-azetidinylmethyl)-4-nitroso-3,4-dihydro-2H-1,4-benzoxazine, 8-methoxy-3-(4-methyl-1-piperazinylmethyl)-4-nitroso-3,4-dihydro-2H-1,4-benzoxazine, 8-methoxy-3-[1-(hexahydro-4H-1,4-diazepinyl)methyl]-4-nitroso-3,4-dihydro-2H-1,4-benzoxazine, 8-chloro-3-aminomethyl-4-nitroso-3,4-dihydro-2H-1,4-benzoxazine, 8-chloro-3-methylaminomethyl-4-nitroso-3,4-dihydro-2H-1,4-benzoxazine, 8-chloro-3-(4-thiomorpholinylmethyl)-4-nitroso-3,4-dihydro-2H-1,4-benzoxazine, 8-chloro-3-(1-pyrrolidinylmethyl)- 4-nitroso-3,4-dihydro-2H-1,4-benzoxazine, 8-chloro-3-(1-azetidinylmethyl)-4-nitroso-3,4-dihydro-2H-1,4-benzoxazine, -chloro-3-(4-methyl-1-piperazinylmethyl)-4-nitroso-3,4-dihydro-2H-1,4-benzoxazine and 8-chloro-3-[1-(hexahydro-4H-1,4-diazepinyl)methyl]-4-nitroso-3,4-dihydro-2H-1,4-benzoxazine, there can be obtained, respectively, 3-(1-piperidinylmethyl)-4-amino-3,4-dihydro-2H-1,4-benzoxazine, 3-(N,N-diethylaminomethyl)-4-amino-3,4-dihydro-2H-1,4-benzoxazine, 8-methoxy-3-aminomethyl-4-amino-3,4-dihydro-2H-1,4-benzoxazine, 8-methoxy-3-methylaminomethyl-4-amino-3,4-dihydro-2H-1,4-benzoxazine, 8-methoxy-3-(4-thiomorpholinylmethyl)-4-amino-3,4-dihydro-2H-1,4-benzoxazine, 8-methoxy-3-(1-pyrrolidinylmethyl)-4-amino-3,4-dihydro-2H-1,4-benzoxazine, 8-methoxy-3-(1-azetidinylmethyl)-4-amino-3,4-dihydro-2H-1,4-benzoxazine, -chloro-3-(4-methyl-1-piperazinylmethyl)-4-amino-3,4-dihydro-2H-1,4-benzoxazine and 8-chloro-3-[1-(hexahydro-4H-1,4-diazepinyl)methyl]-4-amino-3,4-dihydro-2H-1,4-benzoxazine.

Following a procedure similar to that described above in Preparation 3B for the preparation of 2-(4-morpholinylmethyl)-4-amino-3,4-dihydro-2H-1,4-benzoxazine, substituting for the 2-(4-morpholinylmethyl)-4-nitroso-3,4-dihydro-2H-1,4-benzoxazine used therein a molar equivalent amount of 2-(1-piperidinylmethyl)-4-nitroso-3,4-dihydro-2H-1,4-benzoxazine, 2-(N,N-diethylaminomethyl)-4-nitroso-3,4-dihydro-2H-1,4-benzoxazine, 2-aminomethyl-4-nitroso-3,4-dihydro-2H-1,4-benzoxazine, 2-methylaminomethyl-4-nitroso-3,4-dihydro-2H-1,4-benzoxazine, 2-(4-thiomorpholinylmethyl)-4-nitroso-3,4-dihydro-2H-1,4-benzoxazine, 2-(1-pyrrolidinylmethyl)-4-nitroso-3,4-dihydro-2H-1,4-benzoxazine, 2-(1-azetidinylmethyl)-4-nitroso-3,4-dihydro-2H-1,4-benzoxazine, 2-(4-methyl-1-piperazinylmethyl)-4-nitroso-3,4-dihydro-2H-1,4-benzoxazine or 2-[1-(hexahydro-4H-1,4-diazepinyl)methyl]-4-nitroso-3,4-dihydro-2H-1,4-benzoxazine, there can be obtained, respectively, 2-(1-piperidinylmethyl)-4-amino-3,4-dihydro-2H-1,4-benzoxazine, 2-(N,N-diethylaminomethyl)-4-amino-3,4-dihydro-2H-1,4-benzoxazine, 2-aminomethyl-4-amino-3,4-dihydro-2H-1,4-benzoxazine, 2-methylaminomethyl-4-amino-3,4-dihydro-2H-1,4-benzoxazine, 2-(4-thiomorpholinylmethyl)-4-amino-3,4-dihydro-2H-1,4-benzoxazine, 2-(1-pyrrolidinylmethyl)-4-amino-3,4-dihydro-2H-1,4-benzoxazine, 2-(1-azetidinylmethyl)-4-amino-3,4-dihydro-2H-1,4-benzoxazine, 2-(4-methyl-1-piperazinylmethyl)-4-amino-3,4-dihydro-2H-1,4-benzoxazine or 2-[1-(hexahydro-4H-1,4-diazepinyl)methyl]-4-amino-3,4-dihydro-2H-1,4-benzoxazine.

Preparation 4 - The Compounds of Formula V

A. A solution of 37.8 g (0.15 mole) of 3-(4-morpholinylmethyl)-4-amino-3,4-dihydro-2H-1,4-benzoxazine and 25 g (0.15 mole) of phenylthioacetone in 500 ml of glacial acetic acid was heated under reflux for one hour, then cooled, diluted with water and ethyl acetate and then carefully neutralized by the addition of solid sodium carbonate. The two phases were separated, and the aqueous phase was extracted with ethyl acetate. The combined organic extracts were washed with sodium carbonate, then saturated brine, filtered and taken to dryness to give 14.1 g of crude product, about 5 g of which was recrystallized from ethyl acetate/hexane to give 3.2 g of 3-(4-morpholinylmethyl)-5-methyl-6-phenylthio-2,3-dihydropyrrolo[1,2,3-de]-1,4-benzoxazine, m.p. 161°–164° C.

B. Similarly 15.1 g (0.06 mole) of (+)-3-(4-morpholinylmethyl)-4-amino-3,4-dihydro-2H-1,4-benzoxazine was reacted with 12 g (0.07 mole) of phenylthioacetone in 125 ml of glacial acetic acid and the product recrystallized from ethanol to give 8.3 g of (+)-3-(4-morpholinylmethyl)-5-methyl-6-phenylthio-2,3-dihydropyrrolo[1,2,3-de]-1,4-benzoxazine. m.p. 126.5°-127.5° C., $[\alpha]_D^{25} = +53.0°$.

Similarly 2.5 g (0.01 mole) of (−)3-(4-morpholinylmethyl)-4-amino-3,4-dihydro-2H-1,4-benzoxazine was reacted with 1.7 g (0.01 mole) of phenylthioacetone in 25 ml of glacial acetic acid and the product recrystallized from ethanol to give 1.3 g of (−)-3-(4-morpholinylmethyl)-5-methyl-6-phenylthio-2,3-dihydropyrrolo[1,2,3-de]-1,4-benzoxazine. m.p. 127.5°-128.5° C., $[\alpha]_D^{25} = -49.4°$.

Proceeding in a manner similar to that described above in Preparation 4A, substituting for the 3-(4-morpholinylmethyl)-4-amino-3,4-dihydro-2H-1,4-benzoxazine used therein a molar equivalent amount of 3-(1-piperidinylmethyl)-4-amino-3,4-dihydro-2H-1,4-benzoxazine, 3-(N,N-diethylaminomethyl)-4-amino-3,4-dihydro-2H-1,4-benzoxazine, 8-methoxy-3-aminomethyl-4-amino-3,4-dihydro-2H-1,4-benzoxazine, 8-methoxy-3-methylaminomethyl-4-amino-3,4-dihydro-2H-1,4-benzoxazine, 8-methoxy-3-(4-thiomorpholinylmethyl)-4-amino-3,4-dihydro-2H-1,4-benzoxazine, 8-methoxy-3-(1-pyrrolidinylmethyl)-4-amino-3,4-dihydro-2H-1,4-benzoxazine, 8-methoxy-3-(1-azetidinylmethyl)-4-amino-3,4-dihydro-2H-1,4-benzoxazine, 8-methoxy-3-(4-methyl-1-piperazinylmethyl)-4-amino-3,4-dihydro-2H-1,4-benzoxazine, 8-methoxy-3-[1-(hexahydro-4H-1,4-diazepinyl)-methyl]-4-amino-3,4-dihydro-2H-1,4-benzoxazine, 8-chloro-3-aminomethyl-4-amino-3,4-dihydro-2H-1,4-benzoxazine, 8-chloro-3-methylaminomethyl-4-amino-3,4-dihydro-2H-1,4-benzoxazine, 8-chloro-3-(4-thiomorpholinylmethyl)-4-amino-3,4-dihydro-2H-1,4-benzoxazine, 8-chloro-3-(1-pyrrolidinylmethyl)-4-amino-3,4-dihydro-2H-1,4-benzoxazine, 8-chloro-3-(1-azetidinylmethyl)-4-amino-3,4-dihydro-2H-1,4-benzoxazine, 8-chloro-3-(4-methyl-1-piperazinylmethyl)-4-amino-3,4-dihydro-2H-1,4-benzoxazine and 8-chloro-3-[1-(hexahydro-4H-1,4-diazepinyl)methyl]-4-amino-3,4-dihydro-2H-1,4-benzoxazine, there can be obtained, respectively, 3-(1-piperidinylmethyl)-5-methyl-6-phenylthio-2,3-dihydropyrrolo[1,2,3-de]-1,4-benzoxazine, -(N,N-diethylaminomethyl)-5-methyl-6-phenylthio-2,3-dihydropyrrolo[1,2,3-de]-1,4-benzoxazine. 8-methoxy-3-aminomethyl-5-methyl-6-phenylthio-2,3-dihydropyrrolo[1,2,3-de -1,4-benzoxazine. 8-methoxy-3-methylaminomethyl-5-methyl-6-phenylthio-2,3-dihydropyrrolo[1,2,3-de]-1,4-benzoxazine. 8-methoxy-3-(4-thiomorpholinylmethyl)-5-methyl-6-phenylthio-2,3-dihydropyrrolo[1,2,3-de]-1,4-benzoxazine, 8-methoxy-3-(1-pyrrolidinylmethyl)-5-methyl-6-phenylthio-2,3-dihydropyrrolo[1,2,3-de]-1,4-benzoxazine, 8-methoxy-3-(1-azetidinylmethyl)-5-methyl-6-phenylthio-2,3-dihydropyrrolo[1,2,3-de]1,4-benzoxazine. 8-methoxy-3-(4-methyl-1-piperazinylmethyl)-5-methyl-6-phenylthio-2,3-dihydropyrrolo[1,2,3-de]-1,4-benzoxazine, 8-methoxy-3-[1-(hexahydro-4H-1,4-diazepinyl)methyl]-5-methyl-6-phenylthio-2,3-dihydropyrrolo[1,2,3-de]-1,4-benzoxazine, 8-chloro-3-aminomethyl-5-methyl-6-phenylthio-2,3-dihydropyrrolo[1,2,3-de]-1,4-benzoxazine, 8-chloro-3-methylaminomethyl-5-methyl-6-phenylthio-2,3-dihydropyrrolo[1,2,3-de]-1,4-benzoxazine, 8-chloro-3-(4-thiomorpholinylmethyl)-5-methyl-6-phenylthio-2,3-dihydro[1,2,3-de]-1,4-benzoxazine, 8-chloro-3-(1-pyrrolidinylmethyl)-5-methyl-6-phenylthio-2,3-dihydropyrrolo[1,2,3-de]-1,4-benzoxazine, 8-chloro-3-(1-azetidinylmethyl)-5-methyl-6-phenylthio-2,3-dihydropyrrolo[1,2,3-de]-1,4-benzoxazine. 8-chloro-3-(4-methyl-1-piperazinylmethyl)-5-methyl-6-phenylthio-2,3-dihydropyrrolo[1,2,3-de]-1,4-benzoxazine and 8-chloro-3-[1-(hexahydro-4H-1,4-diazepinyl)methyl]-5-methyl-6-phenylthio-2,3-dihydropyrrolo[1,2,3-de]-1,4-benzoxazine.

Proceeding in a manner similar to that described above in Preparation 4A, substituting for the 3-(4-morpholinylmethyl)-4-amino-3,4-dihydro-2H-1,4-benzoxazine used therein a molar equivalent amount of 2-(1-piperidinylmethyl)-4-amino-3,4-dihydro-2H-1,4-benzoxazine, 2-(N,N-diethylaminomethyl)-4-amino-3,4-dihydro-2H-1,4-benzoxazine, 2-aminomethyl-4-amino-3,4-dihydro-2H-1,4-benzoxazine, 2-methylaminomethyl-4-amino-3,4-dihydro-2H-1,4-benzoxazine, 2-(4-thiomorpholinylmethyl)-4-amino-3,4-dihydro-2H-1,4-benzoxazine, 2-(1-pyrrolidinylmethyl)-4-amino-3,4-dihydro-2H-1,4-benzoxazine, 2-(1-azetidinylmethyl)-4-amino-3,4-dihydro-2H-1,4-benzoxazine, 2-(4-methyl-1-piperazinylmethyl)-4-amino-3,4-dihydro-2H-1,4-benzoxazine or 2-[1-(hexahydro-4H-1,4-diazepinyl)methyl]-4-amino-3,4-dihydro-2H-1,4-benzoxazine, there can be obtained, respectively, 2-(1-piperidinylmethyl)-5-methyl-6-phenylthio-2,3-dihydropyrrolo[1,2,3-de]-1,4-benzoxazine, 2-(N,N-diethylaminomethyl)-5-methyl-6-phenylthio-2,3-dihydropyrrolo[1,2,3-de]-1,4-benzoxazine, 2-aminomethyl-5-methyl-6-phenylthio-2,3-dihydropyrrolo[1,2,3-de]-1,4-benzoxazine, 2-methylaminomethyl-5-methyl-6-phenylthio-2,3-dihydropyrrolo[1,2,3-de]-1,4-benzoxazine, 2-(4-thiomorpholinylmethyl)-5-methyl-6-phenylthio-2,3-dihydropyrrolo[1,2,3-de]-1,4-benzoxazine, 2-(1-pyrrolidinylmethyl)-5-methyl-6-phenylthio-2,3-dihydropyrrolo[1,2,3-de]-1,4-benzoxazine, 2-(1-azetidinylmethyl)-5-methyl-6-phenylthio-2,3-dihydropyrrolo[1,2,3-de]-1,4-benzoxazine, 2-(4-methyl-1-piperazinylmethyl)-5-methyl-6-phenylthio-2,3-dihydropyrrolo[1,2,3-de]-1,4-benzoxazine or 2-[1-(hexahydro-4H-1,4-diazepinyl)methyl]-5-methyl-6-phenylthio-2,3-dihydropyrrolo[1,2,3-de]-1,4-benzoxazine.

Preparation 5 - The Compounds of Formula VI

A. To a solution of 10.6 g (0.028 mole) of 3-(4-morpholinylmethyl)-5-methyl-6-phenylthio-2,3-dihydropyrrolo[1,2,3-de]-1,4-benzoxazine in 600 ml of ethanol was added seven teaspoons of Raney nickel. The mixture was heated under reflux for two hours and then filtered through filter aid. Evaporation of the filtrate to dryness and recrystallization of the residue from ethyl acetate afforded 4.7 g of 3-(4-morpholinylmethyl)-5-methyl-2,3-dihydropyrrolo[1,2,3-de]-1,4-benzoxazine, m.p. 178°-180° C.

B. Similarly 7.9 g of (+)-3-(4-morpholinylmethyl)-5-methyl-6-phenylthio-2,3-dihydropyrrolo[1,2,3-de]-1,4-benzoxazine in 300 ml of ethanol was reduced with three teaspoons of Raney nickel to give 5.1 g of (+)-3-(4-morpholinylmethyl)-5-methyl-2,3-dihydropyrrolo[1,2,3-de]-1,4-benzoxazine, $[\alpha]_D^{25} = +64.8°$.

C. Similarly 1.0 g of (−)-3-(4-morpholinylmethyl)-5-methyl-6-phenylthio-2,3-dihydropyrrolo[1,2,3-de]-1,4-benzoxazine in 100 ml of ethanol was reduced with one teaspoon of Raney nickel to give 0.9 g of (−)-3-(4-morpholinylmethyl)-5-methyl-2,3-dihydropyrrolo[1,2,3-de-1,4-benzoxazine, $[\alpha]_D^{25} = -63°$.

Proceeding in a manner similar to that described above in Preparation 5A, substituting for the 3-(4-morpholinylmethyl)-5-methyl-6-phenylthio-2,3-dihydropyrrolo[1,2,3-de]-1,4-benzoxazine used therein a molar equivalent amount of 3-(1-piperidinylmethyl)-5-methyl-6-phenylthio-2,3-dihydropyrrolo[1,2,3-de]-1,4-benzoxazine, 3-(N,N-diethylaminomethyl)-5-methyl-6-phenylthio-2,3-dihydropyrrolo[1,2,3-de]-1,4-benzoxazine, 8-methoxy-3-aminomethyl-5-methyl-6-phenylthio-2,3-dihydropyrrolo[1,2,3-de]-1,4-benzoxazine, 8-methoxy-3-methylaminomethyl-5-methyl-6-phenylthio-2,3-dihydropyrrolo[1,2,3-de]-1,4-benzoxazine, 8-methoxy-3-(4-thiomorpholinylmethyl)-5-methyl-6-phenylthio-2,3-dihydropyrrolo[1,2,3-de]-1,4-benzoxazine, 8-methoxy-3 (1-pyrrolidinylmethyl)-5-methyl-6-phenylthio-2,3-dihydropyrrolo[1,2,3-de]-1,4-benzoxazine, 8-methoxy-3-(1-azetidinylmethyl)-5-methyl-6-phenylthio-2,3-dihydropyrrolo[1,2,3-de]-1,4-benzoxazine, 8-methoxy-3-(4-methyl-1-piperazinylmethyl)-5-methyl-6-phenylthio-2,3-dihydropyrrolo[1,2,3-de]-1,4-benzoxazine, 8-methoxy-3-[1-(hexahydro-4H-1,4-diazepinyl)methyl]-5-methyl-6-phenylthio-2,3-dihydropyrrolo[1,2,3-de]-1,4-benzoxazine, 8-chloro-3-aminomethyl-5-methyl-6-phenylthio-2,3-dihydropyrrolo[1,2,3-de]-1,4-benzoxazine, 8-chloro-3-methylaminomethyl-5-methyl-6-phenylthio-2,3-dihydropyrrolo[1,2,3-de]-1,4-benzoxazine, 8-chloro-3-(4-thiomorpholinylmethyl)-5-methyl-6-phenylthio-2,3-dihydropyrrolo[1,2,3-de]-1,4-benzoxazine, 8-chloro-3-(1-pyrrolidinylmethyl)-5-methyl-6-phenylthio-2,3-dihydropyrrolo[1,2,3-de]-1,4-benzoxazine, 8-chloro- 3-(1-azetidinylmethyl)-5-methyl-6-phenylthio-2,3-dihydropyrrolo[1,2,3-de]-1,4-benzoxazine, 8-chloro-3-(4-methyl-1-piperazinylmethyl)-5-methyl-6-phenylthio-2,3-dihydropyrrolo[1,2,3-de]-1,4-benzoxazine and 8-chloro-3-[1-(hexahydro-4H-1,4-diazepinyl)methyl]-5-methyl-6-phenylthio-2,3-dihydropyrrolo[1,2,3-de]-1,4-benzoxazine, there can be obtained, respectively, 3-(1-piperidinylmethyl)-5-methyl-2,3-dihydropyrrolo[1,2,3-de]-1,4-benzoxazine, 3-(N,N-diethylaminomethyl)-5-methyl-2,3-dihydropyrrolo[1,2,3-de]-1,4-benzoxazine, 8-methoxy-3-aminomethyl-5-methyl-2,3-dihydropyrrolo[1,2,3-de]-1,4-benzoxazine, 8-methoxy-3-methylaminomethyl-5-methyl-2,3-dihydropyrrolo[1,2,3-de]-1,4-benzoxazine, 8-methoxy-3-(4-thiomorpholinylmethyl)-5-methyl-2,3-dihydropyrrolo[1,2,3-de]-1,4-benzoxazine, 8-methoxy-3-(1-pyrrolidinylmethyl)-5-methyl-2,3-dihydropyrrolo[1,2,3-de]-1,4-benzoxazine, 8-methoxy-3-(1-azetidinylmethyl)-5-methyl-2,3-dihydropyrrolo[1,2,3-de]-1,4-benzoxazine, 8-methoxy-3-(4-methyl-1-piperazinylmethyl)-5-methyl-2,3-dihydropyrrolo[1,2,3-de]-1,4-benzoxazine, 8-methoxy-3-[1-(hexahydro-4H-1,4-diazepinyl)methyl]-5-methyl-2,3-dihydropyrrolo[1,2,3-de]-1,4-benzoxazine, 8-chloro-3-aminomethyl-5-methyl-2,3-dihydropyrrolo[1,2,3-de]-1,4-benzoxazine, 8-chloro-3-methylaminomethyl-5-methyl-2,3-dihydropyrrolo[1,2,3-de]-1,4-benzoxazine, 8-chloro-3-(4-thiomorpholinylmethyl)-5-methyl-2,3-dihydropyrrolo[1,2,3-de]-1,4-benzoxazine, 8-chloro-3-(1-pyrrolidinylmethyl)-5-methyl-2,3-dihydropyrrolo[1,2,3-de]-1,4-benzoxazine, 8-chloro-3-(1-azetidinylmethyl)-5-methyl-2,3-dihydropyrrolo[1,2,3-de]-1,4-benzoxazine, 8-chloro-3-( 4-methyl-1-piperazinylmethyl)-5-methyl-2,3-dihydropyrrolo[1,2,3-de]-1,4-benzoxazine and 8-chloro-3-[1-(hexahydro-4H-1,4-diazepinyl)methyl]-5-methyl-2,3-dihydropyrrolo[1,2,3-de]-1,4-benzoxazine.

Proceeding in a manner similar to that described above in Preparation 5A, substituting for the 3-(4-morpholinylmethyl)-5-methyl-6-phenylthio-2,3-dihydropyrrolo[1,2,3-de]-1,4-benzoxazine used therein a molar equivalent amount of 2-(1-piperidinylmethyl)-5-methyl-6-phenylthio-2,3-dihydropyrrolo[1,2,3-de]-1,4-benzoxazine, 2-(N,N-diethylaminomethyl)-5-methyl-6-phenylthio-2,3-dihydropyrrolo[1,2,3-de]-1,4-benzoxazine, 2-aminomethyl-5-methyl-6-phenylthio-2,3-dihydropyrrolo[1,2,3-de]-1,4-benzoxazine, 2-methylaminomethyl-5-methyl-6-phenylthio-2,3-dihydropyrrolo[1,2,3-de]-1,4-benzoxazine, 2-(4-thiomorpholinylmethyl)-5-methyl-6-phenylthio-2,3-dihydropyrrolo[1,2,3-de]-1,4-benzoxazine, 2-(1-pyrrolidinylmethyl)-5-methyl-6-phenylthio-2,3-dihydropyrrolo[1,2,3-de]-1,4-benzoxazine, 2-(1-azetidinylmethyl)-5-methyl-6-phenylthio-2,3-dihydropyrrolo[1,2,3-de]-1,4-benzoxazine, 2-(4-methyl-1-piperazinylmethyl)-5-methyl-6-phenylthio-2,3-dihydropyrrolo[1,2,3-de]-1,4-benzoxazine or 2-[1-(hexahydro-4H-1,4-diazepinyl)methyl]-5-methyl-6-phenylthio-2,3-dihydropyrrolo[1,2,3-de]-1,4-benzoxazine, there can be obtained, respectively, 2-(1-piperidinylmethyl)-5-methyl-2,3-dihydropyrrolo[1,2,3-de]-1,4-benzoxazine, 2-(N,N-diethylaminomethyl)-5-methyl-2,3-dihydropyrrolo[1,2,3-de]-1,4-benzoxazine, 2-aminomethyl- 5-methyl-2,3-dihydropyrrolo[1,2,3-de]-1,4-benzoxazine, 2-methylaminomethyl-5-methyl-2,3-dihydropyrrolo[1,2,3-de]-1,4-benzoxazine, 2-(4-thiomorpholinylmethyl)-5-methyl-2,3-dihydropyrrolo[1,2,3-de]-1,4-benzoxazine, 2-(1-pyrrolidinylmethyl)-5-methyl-2,3-dihydropyrrolo[1,2,3-de]-1,4-benzoxazine, 2-(1-azetidinylmethyl)-5-methyl-2,3-dihydropyrrolo[1,2,3-de]-1,4-benzoxazine, 2-(4-methyl-1-piperazinylmethyl)-5-methyl-2,3-dihydropyrrolo[1,2,3-de]-1,4-benzoxazine or 2-[1-(hexahydro-4H-1,4-diazepinyl)methyl]-5-methyl-2,3-dihydropyrrolo[1,2,3-de]-1,4-benzoxazine.

PREPARATION OF THE FINAL PRODUCTS

Via the Compounds of Formula VI

Example 1

A. To a suspension of 7.5 g (0.056 mole) of aluminum chloride in 100 ml of methylene dichloride (MDC) was added, rapidly with stirring, a solution of 6.2 ml (0.038 mole) of 4-methoxybenzoyl chloride. When addition was complete the mixture was stirred for one hour at room temperature and the resulting solution then added dropwise over a ten minute period with stirring to a solution of 8.5 g (0.031 mole) of 3-(4-morpholinylmethyl)-5-methyl-2,3-dihydropyrrolo-[1,2,3-de]-1,4-benzoxazine in 100 ml of MDC. The resulting mixture was then heated under reflux for thirty minutes, cooled and poured into 300 ml of ice water with stirring. The organic solvent was removed in vacuo, and the residual aqueous medium was diluted with ethyl acetate and neutralized by the addition of saturated aqueous sodium bicarbonate. The organic layer was separated, dried over magnesium sulfate, filtered through silica, taken to dryness in vacuo and chromatographed on silica gel, eluting with 1:1 hexane:ethyl acetate. There was thus obtained about 7 g of crude product which was recrystallized from ethyl acetate/hexane to give 6.0 g of 3-(4-morpholinylmethyl)-5-methyl-6-(4-methoxybenzoyl)-2,3-dihydropyrrolo[1,2,3-de]-1,4-benzoxazine, m.p. 182°–189° C.

B. Following a procedure similar to that described in Example 1A, 3-(4-morpholinylmethyl)-5-methyl-6-(1-naphthylcarbonyl)-2,3-dihydropyrrolo[1,2,3-de]-1,4-benzoxazine methanesulfonate (1.4 g), m.p. 257°–260° C. (from methanol) was prepared by reaction of 2.5 g (0.009 mole) of 3-(4-morpholinylmethyl)-5-methyl-2,3-dihydropyrrolo[1,2,3-de]-1,3-benzoxazine in 50 ml of MDC with 1.9 ml (0.013 mole) of 1-naphthoyl chloride in 50 ml of MDC in the presence of 2.2 g (0.017 mole) of aluminum chloride and recrystallization of the product from methanol/diethyl ether. The free base, recrystallized from ethanol showed m.p. 158.0°–159.0° C.

C. Following a procedure similar to that described in Example 1A, 3-(4-morpholinylmethyl)-5-methyl-6-(6-quinolylcarbonyl)-2,3-dihydropyrrolo[1,2,3-de]-1,4-benzoxazine (3.9 g), m.p. 192°–198° C., was prepared by reaction of 6.9 g (0.025 mole) of 3-(4-morpholinylmethyl)-5-methyl-2,3-dihydropyrrolo-[1,2,3-de]-1,4-benzoxazine in 200 ml of MDC with 11.4 g (0.05 mole) of 6-quinoline carboxylic acid chloride in 100 ml of MDC in the presence of 10 g (0.075 mole) of aluminum chloride and recrystallization of the product from ethyl acetate/hexane.

D. Following a procedure similar to that described in Example 1A, (+)-3-(4-morpholinylmethyl)-5-methyl-6-(5,7-dibromonaphthylcarbonyl)-2,3-dihydropyrrolo[1,2,3-de]-1,4-benzoxazine methanesulfonate (1.98 g), m.p. 256.0–257.0, $[\alpha]_D^{25} = +38.9°$, was prepared by reaction of 4.09 g (0.015 mole) of (+)-3-(4-morpholinylmethyl)-5-methyl-2,3-dihydropyrrolo[1,2,3-de]-1,4-benzoxazine with 5.19 g (0.16 mole) of 5,7-dibromonaphthylcarboxylic acid chloride in 100 ml of MDC in the presence of 15 ml of ethyl aluminum chloride and recrystallization of the product from ethanol.

E. Following a procedure similar to that described above in Example 1A, (−)-3-(4-morpholinylmethyl)-5-methyl-6-(5,7-dibromonaphthylcarbonyl)-2,3-dihydropyrrolo[1,2,3-de]-1,4-benzoxazine methanesulfonate (0.3 g), m.p. 252.0–253.0, $[\alpha]_D^{25} = -35.7°$, was prepared by reaction of 0.63 g (0.002 mole) of (−)-3-(4-morpholinylmethyl)-5-methyl-2,3-dihydropyrrolo[1,2,3-de]-1,4-benzoxazine with 0.88 g (0.0025 mole) of 5,7-dibromonaphthylcarboxylic acid chloride in 15 ml of MDC in the presence of 2.6 ml of ethyl aluminum chloride and crystallization of the product from diethyl ether/ethyl acetate.

Following a procedure similar to that described in Example 1A above, substituting for the 3-(4-morpholinylmethyl)-5-methyl-2,3-dihydropyrrolo[1,2,3-de]used therein a molar equivalent amount of 3-(1-piperidinylmethyl)-5-methyl-2,3-dihydropyrrolo[1,2,3-de]-1,4-benzoxazine, 3-(N,N-diethylaminomethyl)-5-methyl-2,3-dihydropyrrolo[1,2,3-de]-1,4-benzoxazine, 8-methoxy-3-(aminomethyl)-5-methyl-2,3-dihydropyrrolo[1,2,3-de]-1,4-benzoxazine, 8-methoxy-3-methylaminomethyl-5-methyl-2,3-dihydropyrrolo[1,2,3-de]-1,4-benzoxazine, 8-methoxy-3-(4-thiomorpholinylmethyl)-5-methyl-2,3-dihydropyrrolo[1,2,3-de]-1,4-benzoxazine, 8-methoxy-3-(1-pyrrolidinylmethyl)-5-methyl-2,3-dihydropyrrolo[1,2,3-de]-1,4-benzoxazine, 8-methoxy-3-(1-azetidinylmethyl)-5-methyl-2,3-dihydropyrrolo[1,2,3-de]-1,4-benzoxazine, 8-methoxy-3-(4-methyl-1-piperazinylmethyl)-5-methyl-2,3-dihydropyrrolo[1,2,3-de]-1,4-benzoxazine, 8-methoxy-3-[1-(hexahydro-4H-1,4-diazapinyl)methyl]-5-methyl-2,3-dihydropyrrolo[1,2,3-de[-1,4-benzoxazine, 8-chloro-3-aminomethyl-5-methyl-2,3-dihydropyrrolo[1,2,3-de]-1,4-benzoxazine, 8-chloro-3-methylaminomethyl-5-methyl-2,3-dihydropyrrolo[1,2,3-de]-1,4-benzoxazine, 8-chloro-3-(4-thiomorpholinylmethyl)-5-methyl-2,3-dihydropyrrolo-[1,2,3-de]-1,4-benzoxazine, 8-chloro-3-(1-pyrrolidinylmethyl)-5-methyl-2,3-dihydropyrrolo[1,2,3-de]-1,4-benzoxazine, 8-chloro-3-(1-azetidinylmethyl)-5-methyl-2,3-dihydropyrrolo[1,2,3-de]-1,4-benzoxazine, 8-chloro-3-(4-methyl-1-piperzinylmethyl)-5-methyl-2,3-dihydropyrrolo[1,2,3-de]-1,4-benzoxazine and 8-chloro-3-[1-(hexahydro-4H-1,4-diazepinyl)methyl]-5-methyl-2,3-dihydropyrrolo[1,2,3-de]-1,4-benzoxazine, there can be obtained, respectively, 3-(1-piperidinylmethyl)-5-methyl-6-(4-methoxybenzoyl)-2,3-dihydropyrrolo[1,2,3-de]-1,4-benzoxazine, 3-(N,N-diethylaminomethyl)-5-methyl-6-(4-methoxybenzoyl)-2,3-dihydropyrrolo[1,2,3-de]-1,4-benzoxazine, 8-methoxy-3-(aminomethyl)-5-methyl-6-(4-methoxybenzoyl)-2,3-dihydropyrrolo[1,2,3-de]-1,4-benzoxazine, 8-methoxy-3-(methylaminomethyl)-5-methyl-6-(4-methoxybenzoyl)-2,3-dihydropyrrolo[1,2,3-de]-1,4-benzoxazine, 8-methoxy-3-(4-thiomorpholinylmethyl)-5-methyl-6-(4-methoxybenzoyl)-2,3-dihydropyrrolo[1,2,3-de]-1,4-benzoxazine, 8-methoxy-3-(1-pyrrolidinylmethyl)-5-methyl-6-(4-methoxybenzoyl)-2,3-dihydropyrrolo[1,2,3-de]-1,4-benzoxazine, 8-methoxy-3-(1-azetidinylmethyl)-5-methyl-6-(4-methoxybenzoyl)-2,3-dihydropyrrolo[1,2,3-de]-1,4-benzoxazine, 8-methoxy-3-(4-methyl-1-piperazinylmethyl)-5-methyl-6-(4-methoxybenzoyl)-2,3-dihydropyrrolo[1,2,3-de]-1,4-benzoxazine, 8-methoxy-3-[1-(hexahydro-4H-1,4-diazepinyl)methyl]-5-methyl-6-(4-methoxybenzoyl)-2,3-dihydropyrrolo[1,2,3-de]-1,4benzoxazine, 8-chloro-3-aminomethyl-5-methyl-6-(4-methoxybenzoyl)-2,3-dihydropyrrolo[1,2,3-de]-1,4-benzoxazine, 8-chloro-3-methylaminomethyl-5-methyl-6-(4-methoxybenzoyl)-2,3-dihydropyrrolo[1,2,3-de]-1,4-benzoxazine, 8-chloro-3-(4-thiomorpholinylmethyl)-5-methyl-6-(4-methoxybenzoyl)-2,3-dihydropyrrolo[1,2,3-de]-1,4-benzoxazine, 8-chloro-3-(1-pyrrolidinylmethyl)-5-methyl-6-(4-methoxybenzoyl)-2,3-dihydropyrrolo[1,2,3-de]-1,4-benzoxazine, 8-chloro-3-(1-azetidinylmethyl)-5-methyl-6-(4-methoxybenzoyl)-2,3-dihydropyrrolo[1,2,3-de]-1,4-benzoxazine, 8-chloro-3-(4-methyl-1-piperazinylmethyl)-5-methoxybenzoyl)-2,3-dihydropyrrolo[1,2,3-de]-1,4-benzoxazine and 8-chloro-3-[1-(hexahydro-4H-1,4-diazepinyl)methyl]-5-methyl-6-(4-methoxybenzoyl)-2,3-dihydropyrrolo[1,2,3-de]-1,4-benzoxazine.

Ether cleavage of each of the foregoing 8-methoxy-3—$CH_2N=B$-5-methyl-6-(4-methoxybenzoyl)-2,3-dihydropyrrolo[1,2,3-de]-1,4-benzoxazines by heating the latter with pyridine hydrochloride or with aqueous hydrogen bromide affords the corresponding 8-hydroxy-3-$CH_2N=B$-5-methyl-6-(4-hydroxybenzoyl)-2,3-dihydropyrrolo[1,2,3-de]-1,4-benzoxazines.

Following a procedure similar to that described in Example 1A above, substituting for the 3-(4-morpholinylmethyl)-5-methyl-2,3-dihydropyrrolo[1,2,3-de]-1,4-benzoxazine used therein a molar equivalent amount of 2-(1-piperidinylmethyl)-5-methyl-2,3-dihydropyrrolo[1,2,3-de]-1,2,3de]-1,4-benzoxazine, 2-(N,N-diethylaminomethyl)-5-methyl-2,3-dihydropyrrolo[1,2,3-de]-1,4-benzoxazine, 2-(aminomethyl)-5-methyl-2,3-dihydropyrrolo[1,2,3-de]-1,4-benzoxazine, 2-methylaminomethyl-5-methyl-2,3-dihydropyrrolo[1,2,3-de]-1,4-benzoxazine, 2-(4-thiomorpholinylmethyl)-5-methyl-2,3-dihydropyrrolo[1,2,3-de]-1,4-benzoxazine, 2-(1-pyrrolidinylmethyl)-5-methyl-2,3-dihydropyrrolo[1,2,3-de]-1,4-benzoxazine, 2-(1-azetidinylmethyl)-5-methyl-2,3-dihydropyrrolo[1,2,3-de]-1,4-benzoxazine, 2-(4-methyl-1-piperazinylmethyl)-5-methyl-2,3-dihydropyrrolo[1,2,3-de] -1,4-benzoxazine or 2-[1-(hexahydro-4H-1,4-diazepinyl)-methyl]-5-methyl-2,3-dihydropyrrolo[1,4-benzoxazine, there can be obtained, respectively, 2-(1-piperidinylmethyl)-5-methyl-6-(4-methoxybenzoyl)-2,3-dihydropyrrolo[1,2,3-de]-1,4-benzoxazine, 2-(N,N-diethylaminomethyl)-5-methyl-6-(4- methoxybenzoyl)-2,3-dihydropyrrolo[1,2,3-de]-1,4-benzoxazine, 2-(aminomethyl)-5-methyl-6-(4-methoxybenzoyl)-2,3-dihydropyrrolo-[1,2,3-de]-1,4-benzoxazine, 2-methylaminomethyl-5-methyl-6-(4-methoxybenzoyl)-2,3-dihydropyrrolo[1,2,3-de]-1,4-benzoxazine, 2-(4-thiomorpholinylmethyl)-5-methyl-6-(4-methoxybenzoyl)-2,3-dihydropyrrolo[1,2,3-de]-1,4-benzoxazine, 2-(1-pyrrolidinylmethyl)-5-methyl-6-(4-methoxybenzoyl)-2,3-dihydropyrrolo[1,2,3-de]-1,4-benzoxazine, 2-(1-azetidinylmethyl)-5-methyl-6-(4-methoxybenzoyl)-2,3-dihydropyrrolo[1,2,3-de]-1,4-benzoxazine, 2-(4-methyl-1-piperazinylmethyl)-5-methyl-6-(4-methoxybenzoyl)-2,3-dihydropyrrolo[1,2,3-de]-1,4-benzoxazine or 2-[1-(hexahydro-4H-1,4-diazepinyl)methyl]-5-methyl-6-(4-methoxybenzoyl)-2,3-dihydropyrrolo[1,2,3-de]-1,4-benzoxazine.

Via the Compounds of Formula IV

Example 2

A. To a suspension of 8.8 g (0.18 mole) of a 50% dispersion of sodium hydride in hexane was added 1 ml of ethanol followed by the addition, over a period of five minutes, of a solution of 30 g (0.2 mole) of 4-methoxyacetophenone in 50 ml of diethyl ether. 50 ml of ethyl propionate was then added rapidly, and the solution was heated under reflux for three hours and then cooled. An additional 7 g of sodium hydride dispersion was added, the reaction was allowed to subside, and the mixture was then cooled and diluted with 500 ml of water with stirring. The solid which separated was collected by filtration, washed with water, then with diethyl ether and dried in a vacuum oven at 60° C. to give 18.3 g of 5-(4-methoxyphenyl)-3,5-pentanedione as the sodium salt.

A solution of 22.2 g (0.089 mole) of 3-(4-morpholinylmethyl)-4-amino-3,4-dihydro-2H-1,4-benzoxazine and 18.3 g (0.08 mole) of the sodium salt of 5-(4-methoxyphenyl)-3,5-pentanedione in 250 ml of glacial acetic acid was heated under reflux for four hours, then cooled and poured into 1500 ml of water and 600 ml of ethyl acetate. The mixture was neutralized by the addition of solid sodium carbonate and solid sodium bicarbonate with stirring, the organic layer was separated from the aqueous layer and dried over magnesium sulfate, filtered and taken to dryness. The crude product was purified by chromatography on silica gel, eluting with 4:1 hexane/ethyl acetate, the first 700 ml of eluate being discarded, and the next 800 ml, containing the product, being retained. Evaporation of the latter to dryness and recrystallization of the residue from ethyl acetate afforded 3.9 g of 3-(4-morpholinylmethyl)-5-ethyl-6-(4-methoxybenzoyl)-2,3-dihydropyrrolo[1,2,3-de]-1,4-benzoxazine, m.p. 185.5°-187.0° C.

B. Following a procedure similar to that described in Example 2A above, (+)-3-(4-morpholinylmethyl)-5-methyl-6-(1-naphthylcarbonyl)-2,3-dihydropyrrolo[1,2,3-de]-1,4-benzoxazine methanesulfonate (11.6 g from methanol/diethyl ether), m.p. 256°-259° C., $[\alpha]_D^{25} = +40.2°$ (1% in DMF) was prepared by reaction of 15.5 g (0.062 mole) of (+)-3-(4-morpholinylmethyl)-4-amino-3,4-dihydro-2H-1,4-benzoxazine with 15.8 g (0.075 mole) of 4-(1-naphthyl)-2,4-butanedione in 500 ml of toluene in the presence of a catalytic amount of pyridine 3-nitrobenzenesulfonate (the 2,4-diketone being prepared by reaction of methyl 1-naphthyl ketone with ethyl acetate in the presence of sodium hydride and ethanol in diethyl ether), followed by cyclization of the resulting hydrazone by refluxing the latter in 300 ml of glacial acetic acid and recrystallization of the product from methanol/diethyl ether.

Similarly (−)-3-(4-morpholinylmethyl)-5-methyl-6-(1-naphthylcarbonyl)-2,3-dihydropyrrolo[1,2,3-de]-1,4-benzoxazine methanesulfonate (7.2 g), m.p. 256°-260° C., $[\alpha]_D^{25} = -39.4°$ (1% in DMF) was prepared by reaction of 9.3 g (0.037 mole) of (−)-3-(4-morpholinylmethyl)-4-amino-3,4-dihydro-2H-1,4-benzoxazine with 9.5 g (0.045 mole) of 4-(1-naphthyl)-2,4-butanedione in toluene in the presence of a catalytic amount of pyridine 3-nitrobenzenesulfonate followed by cyclization of the resulting hydrazone by refluxing in glacial acetic acid and recrystallization of the product from methanol/diethyl ether.

C. 3-(4-morpholinylmethyl)-6-(4-methoxybenzoyl)-2,3-dihydropyrrolo[1,2,3-de]-1,4-benzoxazine, m.p. 209°-214° C. (1.5 g from ethyl acetate) was prepared by reaction of 13 g (0.052 mole) of 3-(4-morpholinylmethyl)-4-amino-3,4-dihydro-2H-1,4-benzoxazine with 10.2 g (0.057 mole) β-(4-methoxyphenyl)-β-ketopropionaldehyde in glacial acetic acid (the β-ketopropionaldehyde being prepared by reaction of 4-methoxyacetophenone with methyl formate in diethyl ether in the presence of ethanol and sodium hydride).

D. 3-(4-morpholinylmethyl)-5-methyl-6-(2-fluorobenzoyl)-2,3-dihydropyrrolo[1,2,3-de]-1,4-benzoxazine methanesulfonatae, m.p. 241°-245° C. (3.2 g from methanol/diethyl ether) prepared by reaction of 11 g (0.044 mole) of 3-(4-morpholinylmethyl)-4-amino-3,4-dihydro-2H-1,4-benzoxazine with 8.7 g (0.048 mole) of 4-(2-fluorophenyl)-2,4-butanedione in toluene in the presence of a catalytic amount of acid (the 2,4-diketone being prepared by reaction of 2-fluoroacetophenone with ethyl acetate in diethyl ether in the presence of ethanol and sodium hydride).

E. 3-(4-morpholinylmethyl)-5-methyl-6-(4-bromo-1-naphthylcarbonyl)-2,3-dihydropyrrolo[1,2,3-de]-1,4-benzoxazine methanesulfonate, m.p. 281°-286° C. (2.0 g from methanol/diethyl ether) prepared by reaction of 9.5 g (0.038 mole) of 3-(4-morpholinylmethyl)-4-amino-3,4-dihydro-2H-1,4-benzoxazine with 12.2 g (0.042 mole) of 4-(4-bromo-1-naphthyl)-2,4-butanedione in toluene in the presence of a catalytic amount of pyridine toluenesulfonate (the 2,4-diketone being prepared by reaction of 1-acetyl-4-bromonaphthalene with ethyl acetate in diethyl ether in the presence of ethanol and sodium hydride) followed by cyclization of the resulting hydrazone by refluxing in glacial acetic acid.

F. 3-(4-morpholinylmethyl)-6-(1-naphthylcarbonyl)-2,3-dihydropyrrolo[1,2,3-de]-1,4-benzoxazine, m.p. 190°-193° C. (2.6 g from ethyl acetate) prepared by reaction of 10.7 g (0.04 mole) of 3-(4-morpholinylmethyl)-4-amino-3,4-dihydro-2H-1,4-benzoxazine with 9.4 g (0.048 mole) of β-(1-naphthyl)-β-ketopropionaldehyde in toluene in the presence of a catalytic amount of pyridine toluenesulfonate (the β-ketopropionaldehyde being prepared by reaction of 1-acetylnaphthalene with methyl formate in diethyl ether in the presence of ethanol and sodium hydride) followed by cyclization of the resulting hydrazone by refluxing in glacial acetic acid.

G. (+)-3-(4-morpholinylmethyl)-5-methyl-6-(5,7-dibromo-1-naphthylcarbonyl)-2,3-dihydropyrrolo[1,2,3-de]-1,4-benzoxazine m.p. 120° C. (239 mg), $[\alpha]_D^{25} = +44.4°$ (CHCl₃), prepared by reaction of 1.4 g (0.0056 mole) of (+)-3-(4-morpholinylmethyl)-4-amino-3,4-dihydro-2H-1,4-benzoxazine with 1.9 g (0.0051 mole) of 4-(5,7-dibromo-1-naphthyl)-2,4-butanedione in toluene in the presence of a catalytic amount of pyridine 3-nitrobenzenesulfonate (the diketone being prepared by reaction of 1-acetyl-5,7-dibromonaphthalene with ethyl acetate in diethyl ether in the presence of ethanol and sodium hydride) followed by cyclization of the resulting hydrazone in refluxing glacial acetic acid.

The 1-acetyl-5,7-dibromonaphthalene used in the foregoing procedure was prepared by dibromination of benz[cd]indol-2-(1H)-one with bromine in glacial acetic acid to give 41 g of 6,8-dibromobenz[cd]indol-2(1H)-one, m.p. 259°-260° C. The latter (12.8 g) was heated under reflux for one hour in two liters of 5% potassium hydroxide, the reaction mixture was cooled, filtered and then treated with 28 g of a solution of sodium nitrite in 50 ml of water. The resulting solution, cooled to 0° C., was added dropwise to 800 ml of a 40% solution of sulfuric acid while maintaining the temperature at −5° C. The reaction mixture was stirred for one hour, then poured slowly into a solution of 140 g of sodium hypophosphite in 800 ml of water at 0° C. with stirring. The solid which separated was collected by filtration and dissolved in 3 liters of 2% sodium carbonate solution, and the resulting solution was filtered, acidified with concentrated hydrochloric acid and the mixture extracted with ethyl acetate. The combined organic extracts were dried and taken to dryness to give 8 g of 5,7-dibromo-1-naphthalenecarboxylic acid which was heated with thionyl chloride in the presence of a small amount of DMF. The resulting crude 5,7-dibromo-1-naphthalenecarboxylic acid chloride, together with 6.0 g of methoxymethylamine hydrochloride in 750 ml of MDC, was treated dropwise at 0° C. with 60 ml of tirethylamine in 250 ml of MDC. The reaction mixture was filtered, the filtrate was taken to dryness, and the resulting residue (12.0 g) was dissolved in THF and treated at 0° C. with stirring with a solution of 29.5 ml of 3M methyl magnesium bromide. The reaction mixture was stirred for ten minutes, quenched with water, taken to dryness and the residue partitioned between ethyl acetate and water. The mixture was filtered, the organic extracts were separated, dried and taken to dryness to give 9.9 g of 1-acetyl-5,7-dibromonaphthalene.

H. (−)-3-(4-morpholinylmethyl)-5-methyl-6-(4-methoxybenzoyl)-2,3-dihydropyrrolo[1,2,3-de]-1,4-benzoxazine, m.p. 149°-150° C. (3.7 g from diethyl ether), $[\alpha]_D^{25} = -53.8°$ (1% in CHCl$_3$), prepared by reaction of 5.8 g (0.023 mole) of (−)-3-(4-morpholinylmethyl)-4-amino-3,4-dihydro-2H-1,4-benzoxazine with 5.0 g (0.026 mole) of 4-(4-methoxyphenyl)-2,4-butanedione in toluene in the presence of a catalytic amount of pyridine 3-nitrobenzenesulfonate (the diketone being prepared by reaction of 4-methoxyacetophenone with ethyl acetate in diethyl ether in the presence of ethanol and sodium hydride) followed by cyclization of the resulting hydrazone in refluxing glacial acetic acid.

Similarly (+)-3-(4-morpholinylmethyl)-5-methyl-6-(4-methoxybenzoyl)-2,3-dihydropyrrolo[1,2,3-de]-1,4-benzoxazine, m.p. 152°-153° C. (3.88 g from diethyl ether), $[\alpha]_D^{25} = +55.1°$ (1% in CHCl$_3$), was prepared by reaction of 5.84 g (0.023 mole) of (+)-3-(4-morpholinylmethyl)-4-amino-3,4-dihydro-2H-1,4-benzoxazine with 5.0 g (0.026 mole) of 4-(4-methoxyphenyl)-2,4-butanedione in toluene in the presence of a catalytic amount of pyridine 3-nitrobenzenesulfonate followed by cyclization of the resulting hydrazone in refluxing glacial acetic acid.

I. 2-(4-morpholinylmethyl)-5-methyl-6-(1-naphthylcarbonyl)-2,3-dihydropyrrolo[1,2,3-de]-1,4-benzoxazine, m.p. 158°-159° C. (2.1 g from ethanol), prepared by reaction of 4.6 g (0.019 mole) of 2-(4-morpholinylmethyl)-4-amino-3,4-dihydro-2H-1,4-benzoxazine with 4.0 g (0.019 mole) of 4-(1-naphthyl)-2,4-butanedione in 50 ml of glacial acetic acid.

Proceeding in a manner similar to that described in Example 2A above, substituting for the 5-(4-methoxyphenyl)-3,5-pentanedione used therein a molar equivalent amount of 4-(4-methylphenyl)-2,4-butanedione, 4-(4-methylmercaptophenyl)-2,4-butanedione, 4-(4-methylsulfinylphenyl)-2,4-butanedione, 4-(4-methylsulfonylphenyl)-2,4-butanedione, 4-(3,4-methylenedioxyphenyl)-2,4-butanedione, 4-(2-naphthyl)-2,4-butanedione, 4-(7-methyl-2-naphthyl)-2,4-butanedione, 4-(7-methoxy-2-naphthyl)-2,4-butanedione, 4-(7-methylmercapto-2-naphthyl)-2,4-butanedione, 4-(7-methylsulfinyl-2-naphthyl)-2,4-butanedione, 4-(7-methylsulfonyl-2-naphthyl)-2,4-butanedione, 4-(2-quinolyl)-2,4-butanedione, 4-(3-quinolyl)-2,4-butanedione, 4-(4-quinolyl)-2,4-butanedione, 4-(5-quinolyl)-2,4-butanedione, 4-(7-quinolyl)-2,4-butanedione or 4-(8-quinolyl)-2,4-butanedione, there can be obtained, respectively, 3-(4-morpholinylmethyl)-5-methyl-6-(4-methylbenzoyl)-2,3-dihydropyrrolo[1,2,3-de]-1,4-benzoxazine, 3-(4-morpholinylmethyl)-5-methyl-6-(4-methylmercaptobenzoyl)-2,3-dihydropyrrolo[1,2,3-de]-1,4-benzoxazine, 3-(4-morpholinylmethyl)-5-methyl-6-(4-methylsulfinylbenzoyl)-2,3-dihydropyrrolo[1,2,3-de] -1,4-benzoxazine, 3-(4-morpholinylmethyl)-5-methyl-6-(4-methylsulfonylbenzoyl)-2,3-dihydropyrrolo[1,2,3-de]-1,4-benzoxazine, 3-(4-morpholinylmethyl)-5-methyl-6-(3,4-methylenedioxybenzoyl)-2,3-dihydropyrrolo[1,2,3-de]-1,4-benzoxazine, 3-(4-morpholinylmethyl)-5-methyl-6-(2-naphthylcarbonyl)-2,3-dihydropyrrolo[1,2,3-de]-1,4-benzoxazine, 3-(4-morpholinylmethyl)-5-methyl-6-(7-methyl-2-naphthylcarbonyl)-2,3-dihydropyrrolo[1,2,3-de]-1,4-benzoxazine, 3-(4-morpholinylmethyl)-5-methyl-6-(7-methoxy-2-naphthylcarbonyl)-2,3-dihydropyrrolo[1,2,3-de]-1,4-benzoxazine, 3-(4-morpholinylmethyl)-5-methyl-6-(7-methylmercapto-2-naphthylcarbonyl)-2,3-dihydropyrrolo[1,2,3-de]-1,4-benzoxazine, 3-(4-morpholinylmethyl)-5-methyl-6-(7-methylsulfinyl-2-naphthylcarbonyl)-2,3-dihydropyrrolo[1,2,3-de]-1,4-benzoxazine, 3-(4-morpholinylmethyl)-5-methyl-6-(7-methylsulfonyl-2-naphthylcarbonyl)-2,3-dihydropyrrolo[1,2,3-de]-1,4-benzoxazine, 3-(4-morpholinylmethyl)-5-methyl-6-(2-quinolylcarbonyl)-2,3-dihydropyrrolo[1,2,3-de]-1,4-benzoxazine, 3-(4-morpholinylmethyl)-5-methyl-6-(3-quinolylcarbonyl)-2,3-dihydropyrrolo[1,2,3-de]-1,4-benzoxazine, 3-(4-morpholinylmethyl)-5-methyl-6-(4-quinolylcarbonyl)-2,3-dihydropyrrolo[1,2,3-de]-1,4-benzoxazine, 3-(4-morpholinylmethyl)-5-methyl-6-(5-quinolylcarbonyl)-2,3-dihydropyrrolo[1,2,3-de]-1,4-benzoxazine, 3-(4-morpholinylmethyl)-5-methyl-6-(7-quinolylcarbonyl)-2,3-dihydropyrrolo[1,2,3-de]-1,4-benzoxazine and 3-(4-morpholinylmethyl)-5-methyl-6-(8-quinolylcarbonyl)-2,3-dihydropyrrolo[1,2,3-de]-1,4-benzoxazine.

Ether cleavage of the foregoing 3-(4-morpholinylmethyl)-5-methyl-6-(4-methoxybenzoyl)-2,3-dihydropyrrolo[1,2,3-de]-1,4-benzoxazine and 3-(4-morpholinylmethyl)-5-methyl-6-(7-methoxy-2-naphthylcarbonyl)-2,3-dihydropyrrolo-8 1,2,3-de]-1,4-benzoxazine by heating the latter with pyridine hydrochloride or with aqueous hydrogen bromide affords, respectively, 3-(4-morpholinylmethyl)-5-methyl-6-(4-hydroxybenzoyl)-2,3- dihydropyrrolo[1,2,3-de]-1,4-benzoxazine and 3-(4-morpholinylmethyl)-5-methyl-6-(7-hydroxy-2-naphthylcarbonyl)-2,3-dihydropyrrolo[1,2,3-de]-1,4-benzoxazine.

Proceeding in a manner similar to that described in Example 2A above, substituting for the 3-(4-morpholinylmethyl)-4-amino-3,4-dihydro-2H-1,4-benzoxazine used therein a molar equivalent amount of 2-(1-piperidinylmethyl)-4-amino-3,4-dihydro-2H-1,4-benzoxazine, 2-(N,N-diethylaminomethyl)-4-amino-3,4-dihydro-2H-1,4-benzoxazine, 2-aminomethyl-4-amino-3,4-dihydro-2H-1,4-benzoxazine, 2-methylaminomethyl-4-amino-3,4-dihydro-2H-1,4-benzoxazine, 2-(4-thiomorpholinylmethyl)-4-amino-3,4-dihydro-2H-1,4-benzoxazine, 2-(1-pyrrolidinylmethyl)-4-amino-3,4-dihydro-2H-1,4-benzoxazine, 2-(1-azetidinylmethyl)-4-amino-3,4-dihydro-2H-1,4-benzoxazine, 2-(4-methyl-1-piperazinylmethyl)-4-amino-3,4-dihydro-2H-1,4-benzoxazine or 2-[1-(hexahydro-4H-1,4-diazepinyl)methyl]-4-amino-3,4-dihydro-2H-1,4-benzoxazine, and substituting for the 5-(4-methoxyphenyl)-3,5-pentanedione used therein a molar equivalent amount of 4-(1-naphthyl)-2,4-butanedione, there can be obtained, respectively, 2-(1-piperidinylmethyl)-5-methyl-6-(1-naphthylcarbonyl)-2,3-dihydropyrrolo[1,2,3-de]-1,4-benzoxazine, 2-(N,N-diethylaminomethyl)-5-methyl-6-(1-naphthylcarbonyl)-2,3-dihydropyrrolo[1,2,3-de]-1,4-benzoxazine, 2-(aminomethyl)-5-methyl-6-(1-naphthylcarbonyl)-2,3-dihydropyrrolo[1,2,3-de]-1,4-benzoxazine, 2-(methylaminomethyl)-5-methyl-6-(1-naphthylcarbonyl)-2,3-dihydropyrrolo[1,2,3-de]-1,4-benzoxazine, 2-(4-thiomorpholinylmethyl)-5-methyl-6-(1-naphthylcarbonyl)-2,3-dihydropyrrolo[1,2,3-de]-1,4-benzoxazine, 2-(1-pyrrolidinylmethyl)-5-methyl-6-(1-naphthylcarbonyl)-2,3-dihydropyrrolo[1,2,3-de]-1,4-benzoxazine, 2-(1-azetidinylmethyl)-5-methyl-6-(1-naphthylcarbonyl)-2,3-dihydropyrrolo[1,2,3-de]-1,4-benzoxazine, 2-(4-methyl-1-piperazinylmethyl)-5-methyl-6-(1-naphthylcarbonyl)-2,3-dihydropyrrolo[1,2,3-de]-1,4-benzoxazine or 2-[1-(hexahydro-4H-1,4-diazepinyl)methyl]-5-methyl-6-(1-naphthylcarbonyl)-2,3-dihydropyrrolo[1,2,3-de]-1,4-benzoxazine.

BIOLOGICAL TEST RESULTS

Data obtained with the compounds of the invention in the acetylcholine-induced abdominal constriction test (ACH) (expressed as the $ED_{50}$ in mg/kg or as the percent inhibition at a given dose level), the anti-bradykinin test (BDK) (expressed as the $ED_{50}$ or as the percent inhibition at a given dose level), the acetic acid-induced writhing assay in the rat (RW) (expressed as the $ED_{50}$ or the percent inhibition at a given dose level), the inhibition of cyclooxygenase assay (CO) (expressed as the percent inhibition at a given dose level, e.g. 19% I at 30 μM) and the Randall-Selitto (RS) paw pressure test (expressed as the minimum effective dose, MED, in mg/kg $ED_{50}$) are given in the table below. Negative values in the cyclooxygenase inhibition assay indicate increases in cyclooxygenase activity over controls that have not been demonstrated to differ significantly from controls. In the acetylcholine-induced abdominal constriction test, the test compounds were administered either as suspensions in gum tragacanth (GT) or as aqueous solutions prepared by addition of just sufficient dilute aqueous methanesulfonic acid (MS) or dilute aqueous lactic acid (LA) to dissolve the compound. The compounds are identified by the example number above where their preparations are described. All data in the anti-bradykinin, rat writhing and Randall-Selitto tests were obtained on oral administration.

| Ex. | ACH i.v. | ACH p.o. | ACH s.c. | BRKD | RW | CO | R-S |
|---|---|---|---|---|---|---|---|
| 1A | 3.4 | 20%/100 (GT) 30%/100 (MS) | | 0%/300 | 23%/300 50.6%/100 | 30 μM/19% I | |
| 1B (d,l) | 0.25 | 30%/100 (GT) 33 (MS) | 73%/100 | 35.0 | 8.6 | 30 μM/−35% I | 0.003 |
| 2B (d) | 0.027 | 33 (MS) | | | 7.5 | 100 μM/9% I | |
| 2B (l) | 30%/5.5 10%/3 40%/1 20%/0.3 | 30%/173 (MS) 10%/100,30 (MS) 10%/10 (MS) | | | 12%/100 | 100 μM/10.4% I | |
| 1C | 1.8 | 27 | 0%/100 (GT) | | 3.5 | 30 μM/−26.2% I | |
| 2A (d,l) | | 20%/100 (GT) | | | | | |
| 2C | 3.9 | 30%/100 (GT) | | | | 30 μM/−8.9% I | |
| 2D | 2.0 | 30%/100 (MS) | | | | | |
| 2E | | 35%/100 (GT) 0%/100 (LA) | | | | | |
| 2F | | 10%/100 (GT) | | | | | |

Data obtained on the compounds of the invention in the mouse vas deferens adrenergic transmission test (MVD) expressed as the $IC_{50}$ in μM (the inhibitory concentration which produces 50% of the maximum response) or as the percent inhibition at a given does level are given in the table below. As before, the compounds are identified by the example number above where their preparations are described.

| Ex. | MVD |
|---|---|
| 1A | 0.123 ± 0.013 |
| 1B (base) | 0.004 ± 0.002 |
| 1B (CH$_3$SO$_3$H) | 0.006 ± 0.0006 |
| 1C | 0.021 ± 0.00065 |
| 1E | 2.62 ± 1.7 |
| 2A | >10 (27%/10 μM) |
| 2B (d) | 0.00043 ± 0.0001 |
| 2B (l) | >10 (37%/10 μM) |
| 2C | 0.044 ± 0.0098 |
| 2D | 0.076 ± 0.004 |
| 2E | 0.0022 ± 0.0002 |
| 2F | 0.002 ± 0.00003 |
| 2G | 0.04 ± 0.0054 |
| 2H (l) | >10 (44%/10 μM) |
| 2H (d) | 0.044 ± 0.013 |
| 2I | 0.004 ± 0.002 |

We claim:

1. A member of the group consisting of (A) compounds having the formula

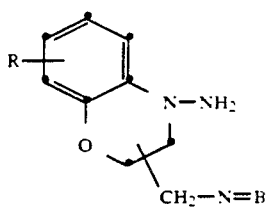

where:

R is hydrogen or from one to two substituents selected from the group consisting of lower-alkyl, lower-alkoxy, hydroxy or halogen in the 6-, 7-, or 8-positions; and N=B is amino, N-lower-alkylamino, N,N-di-lower-alkylamino, 4-morpholinyl, 4-thiomorpholinyl, 1-piperidinyl, 1-pyrrolidinyl, 1-azetidinyl, 4-lower-alkyl-1-piperazinyl or 1-(hexahydro-4H-1,4-diazepinyl);

(B) acid-addition salts thereof; and (C) racemic mixtures and the d- and l-enantiomers thereof.

2. A compound according to claim 1 where R is hydrogen and N=B is 4-morpholinyl.

* * * * *